United States Patent
Hopkins et al.

(10) Patent No.: US 11,587,657 B2
(45) Date of Patent: Feb. 21, 2023

(54) METHOD, APPARATUS, AND COMPUTER PROGRAM PRODUCT FOR PERFORMING AN ALTERNATIVE EVALUATION PROCEDURE IN RESPONSE TO AN ELECTRONIC MESSAGE

(71) Applicant: McKesson Corporation, Irving, TX (US)

(72) Inventors: Stacy Hopkins, Tucker, GA (US); Stewart Aragon, Hadley, MA (US); Keith Crozier, North Kingstown, RI (US)

(73) Assignee: MCKESSON CORPORATION, Irving, TX (US)

( * ) Notice: Subject to any disclaimer, the term of this patent is extended or adjusted under 35 U.S.C. 154(b) by 77 days.

(21) Appl. No.: 17/012,565

(22) Filed: Sep. 4, 2020

(65) Prior Publication Data

US 2022/0076797 A1    Mar. 10, 2022

(51) Int. Cl.
*G16H 20/10* (2018.01)
*G06Q 10/10* (2012.01)
*G16H 10/60* (2018.01)
*G06F 40/205* (2020.01)

(52) U.S. Cl.
CPC .......... *G16H 20/10* (2018.01); *G06F 40/205* (2020.01); *G06Q 10/10* (2013.01); *G16H 10/60* (2018.01)

(58) Field of Classification Search
CPC ............................................... G06Q 50/20–26
See application file for complete search history.

(56) References Cited

U.S. PATENT DOCUMENTS

| 5,012,035 A | 4/1991 | Sartori et al. |
| 5,173,851 A | 12/1992 | Off et al. |
| 5,595,342 A | 1/1997 | McNair et al. |
| 5,628,530 A | 5/1997 | Thornton |
| 5,726,092 A | 3/1998 | Mathews et al. |

(Continued)

FOREIGN PATENT DOCUMENTS

| AU | 2003243327 A | 12/2003 |
| CA | 2 482 370 A1 | 3/2006 |

(Continued)

OTHER PUBLICATIONS

United States Patent and Trademark Office, Advisory Action received for U.S. Appl. No. 16/832,318, dated Jan. 28, 2022, 4 pages, U.S.

(Continued)

*Primary Examiner* — Neal Sereboff
(74) *Attorney, Agent, or Firm* — Alston & Bird LLP

(57) ABSTRACT

A method, apparatus and computer program product are provided for parsing a message received from a requesting computer to identify an indication of a transaction, an entity identifier, and an identifier of a first evaluation system. The entity identifier is evaluated based on historical data and/or eligibility data to determine an alternative evaluation procedure. The alternative evaluation procedure is preformed to obtain response information regarding the transaction, that may differ from response information otherwise obtained via the first evaluation system. A response to the message is constructed that includes the response information and is transmitted to the requesting computer.

14 Claims, 2 Drawing Sheets

(56) References Cited

U.S. PATENT DOCUMENTS

| | | | |
|---|---|---|---|
| 5,757,898 A | 5/1998 | Nishikawa | |
| 5,769,228 A | 6/1998 | Wroblewski | |
| 6,012,035 A | 1/2000 | Freeman et al. | |
| 6,111,218 A | 8/2000 | Akers et al. | |
| 6,463,462 B1 | 10/2002 | Smith et al. | |
| 6,595,342 B1 | 7/2003 | Maritzen et al. | |
| 6,726,092 B2 | 4/2004 | Goldberg et al. | |
| 6,757,898 B1 | 6/2004 | Ilsen et al. | |
| 6,769,228 B1 | 8/2004 | Mahar | |
| 7,155,397 B2 | 12/2006 | Alexander et al. | |
| 7,192,741 B2 | 3/2007 | Otte et al. | |
| 7,337,129 B1 | 2/2008 | Lowry et al. | |
| 7,346,768 B2 | 3/2008 | DiRienzo | |
| 7,409,632 B1 | 8/2008 | DiRienzo | |
| 7,734,483 B1 | 6/2010 | Smith et al. | |
| 7,783,383 B2 | 8/2010 | Eliuk et al. | |
| 7,840,424 B2 | 11/2010 | Wiley et al. | |
| 7,856,364 B1 | 12/2010 | Wiley et al. | |
| 7,912,741 B1 | 3/2011 | Pinsonneault | |
| 7,921,021 B1 | 4/2011 | Newman | |
| 8,036,913 B1 | 10/2011 | Pinsonneault et al. | |
| 8,036,914 B1 | 10/2011 | Pinsonneault | |
| 8,036,918 B1 | 10/2011 | Pinsonneault | |
| 8,050,943 B1 | 11/2011 | Wiley et al. | |
| 8,060,379 B1 | 11/2011 | Pinsonneault et al. | |
| 8,326,773 B1 | 12/2012 | Bellamy | |
| 8,412,537 B1 | 4/2013 | Fenton et al. | |
| 8,489,415 B1 | 7/2013 | Ringold | |
| 8,521,557 B1 | 8/2013 | Ringold et al. | |
| 8,560,340 B1 | 10/2013 | Ringold | |
| 8,645,162 B2 | 2/2014 | Boerger et al. | |
| 8,671,018 B2 | 3/2014 | Thomas et al. | |
| 8,738,399 B1 | 5/2014 | Abou Nader et al. | |
| 8,786,650 B1 | 7/2014 | Eller et al. | |
| 8,984,059 B2 | 3/2015 | Johnson | |
| 9,026,507 B2 | 5/2015 | Shraim et al. | |
| 9,100,793 B2 | 8/2015 | Johnson | |
| 9,171,322 B2 | 10/2015 | Spievak et al. | |
| 9,356,947 B2 | 5/2016 | Shraim et al. | |
| 9,760,871 B1 | 9/2017 | Pourfallah et al. | |
| 10,157,262 B1 | 12/2018 | Pinsonneault | |
| 10,417,380 B1 | 9/2019 | Kaye et al. | |
| 10,489,552 B2 | 11/2019 | Pinsonneault | |
| 10,496,793 B1 | 12/2019 | Lawrence et al. | |
| 10,565,656 B1 * | 2/2020 | Pinsonneault | G06Q 30/0207 |
| 10,606,984 B1 | 3/2020 | Kaye et al. | |
| 10,616,146 B1 | 4/2020 | Hopkins et al. | |
| 10,628,797 B2 | 4/2020 | Shraim et al. | |
| 10,642,812 B1 | 5/2020 | Hopkins et al. | |
| 10,713,694 B1 | 7/2020 | Harris et al. | |
| 10,747,848 B2 | 8/2020 | Guinan | |
| 10,778,618 B2 | 9/2020 | Karnin et al. | |
| 10,924,545 B2 | 2/2021 | Momchilov et al. | |
| 10,924,585 B1 | 2/2021 | Harris et al. | |
| 10,929,932 B1 | 2/2021 | Golden et al. | |
| 10,978,198 B1 | 4/2021 | Pinsonneault | |
| 10,999,224 B1 | 5/2021 | Frechen et al. | |
| 2001/0029483 A1 | 10/2001 | Schultz et al. | |
| 2001/0037216 A1 | 11/2001 | Oscar et al. | |
| 2001/0039589 A1 | 11/2001 | Aho et al. | |
| 2001/0056359 A1 | 12/2001 | Abreu | |
| 2002/0002495 A1 | 1/2002 | Ullman | |
| 2002/0004812 A1 | 1/2002 | Motoyama | |
| 2002/0032582 A1 | 3/2002 | Feeney et al. | |
| 2002/0032583 A1 | 3/2002 | Joao | |
| 2002/0035484 A1 | 3/2002 | McCormick | |
| 2002/0087583 A1 | 7/2002 | Morgan et al. | |
| 2002/0111832 A1 | 8/2002 | Judge | |
| 2002/0147614 A1 | 10/2002 | Doerr et al. | |
| 2002/0188552 A1 | 12/2002 | Kavounas et al. | |
| 2002/0198831 A1 | 12/2002 | Patricelli et al. | |
| 2003/0009367 A1 | 1/2003 | Morrison | |
| 2003/0050796 A1 | 3/2003 | Baldwin | |
| 2003/0050799 A1 | 3/2003 | Jay et al. | |
| 2003/0069760 A1 | 4/2003 | Gelber | |
| 2003/0074234 A1 | 4/2003 | Stasny | |
| 2003/0097310 A1 | 5/2003 | Ono et al. | |
| 2003/0149625 A1 | 8/2003 | Leonardi et al. | |
| 2003/0154163 A1 | 8/2003 | Phillips et al. | |
| 2003/0172008 A1 | 9/2003 | Hage et al. | |
| 2003/0187690 A1 | 10/2003 | Miller | |
| 2003/0229540 A1 | 12/2003 | Algiene | |
| 2003/0236747 A1 | 12/2003 | Sager | |
| 2004/0039599 A1 | 2/2004 | Fralic | |
| 2004/0054685 A1 | 3/2004 | Rahn et al. | |
| 2004/0059607 A1 | 3/2004 | Ball et al. | |
| 2004/0073456 A1 | 4/2004 | Gottlieb et al. | |
| 2004/0073457 A1 | 4/2004 | Kalies | |
| 2004/0078222 A1 | 4/2004 | Khan et al. | |
| 2004/0078234 A1 | 4/2004 | Tallal, Jr. | |
| 2004/0088187 A1 | 5/2004 | Chudy et al. | |
| 2004/0103062 A1 | 5/2004 | Wood et al. | |
| 2004/0117323 A1 | 6/2004 | Mindala | |
| 2004/0148198 A1 | 7/2004 | Kalies | |
| 2004/0153336 A1 | 8/2004 | Virdee et al. | |
| 2004/0199545 A1 | 10/2004 | Wagner et al. | |
| 2004/0236630 A1 | 11/2004 | Kost et al. | |
| 2004/0249745 A1 | 12/2004 | Baaren | |
| 2005/0015280 A1 | 1/2005 | Gabel et al. | |
| 2005/0060201 A1 | 3/2005 | Connely, III et al. | |
| 2005/0075932 A1 | 4/2005 | Mankoff | |
| 2005/0080692 A1 | 4/2005 | Padam et al. | |
| 2005/0102169 A1 | 5/2005 | Wilson | |
| 2005/0154627 A1 | 7/2005 | Zuzek et al. | |
| 2005/0187793 A1 | 8/2005 | Myles | |
| 2005/0197862 A1 | 9/2005 | Paterson et al. | |
| 2005/0240442 A1 | 10/2005 | Lapsker et al. | |
| 2005/0240473 A1 | 10/2005 | Ayers, Jr. et al. | |
| 2005/0261939 A1 | 11/2005 | Augspurger et al. | |
| 2005/0288972 A1 | 12/2005 | Marvin et al. | |
| 2006/0020514 A1 | 1/2006 | Yered | |
| 2006/0026041 A1 | 2/2006 | Ullman | |
| 2006/0036470 A1 | 2/2006 | Oaks | |
| 2006/0085231 A1 | 4/2006 | Brofman | |
| 2006/0085385 A1 | 4/2006 | Foster et al. | |
| 2006/0113376 A1 | 6/2006 | Reed et al. | |
| 2006/0149595 A1 | 7/2006 | Williams et al. | |
| 2006/0149784 A1 | 7/2006 | Tholl et al. | |
| 2006/0184391 A1 | 8/2006 | Barre et al. | |
| 2006/0212318 A1 | 9/2006 | Dooley | |
| 2006/0212345 A1 | 9/2006 | Soza et al. | |
| 2006/0224414 A1 | 10/2006 | Astrup et al. | |
| 2006/0224417 A1 | 10/2006 | Werner | |
| 2006/0224443 A1 | 10/2006 | Soza et al. | |
| 2006/0235747 A1 | 10/2006 | Hammond et al. | |
| 2006/0259363 A1 | 11/2006 | Jhetam et al. | |
| 2007/0005402 A1 | 1/2007 | Kennedy et al. | |
| 2007/0033137 A1 | 2/2007 | Provost et al. | |
| 2007/0043589 A1 | 2/2007 | Warren et al. | |
| 2007/0043595 A1 | 2/2007 | Pederson | |
| 2007/0050209 A1 | 3/2007 | Yered | |
| 2007/0050210 A1 | 3/2007 | Wiley | |
| 2007/0067186 A1 | 3/2007 | Brenner et al. | |
| 2007/0094133 A1 | 4/2007 | Anandarao et al. | |
| 2007/0108053 A1 | 5/2007 | Cramer et al. | |
| 2007/0136100 A1 | 6/2007 | Daugherty et al. | |
| 2007/0162303 A1 | 7/2007 | Wiley et al. | |
| 2007/0185799 A1 | 8/2007 | Harrison et al. | |
| 2007/0191985 A1 | 8/2007 | Bain | |
| 2007/0194352 A1 | 8/2007 | Han | |
| 2007/0202886 A1 | 8/2007 | Dhebri et al. | |
| 2007/0204043 A1 | 8/2007 | Espinosa et al. | |
| 2007/0219813 A1 | 9/2007 | Moore | |
| 2007/0233525 A1 | 10/2007 | Boyle | |
| 2007/0233526 A1 | 10/2007 | Hoffman et al. | |
| 2007/0239493 A1 | 10/2007 | Sweetland et al. | |
| 2007/0250341 A1 | 10/2007 | Howe et al. | |
| 2007/0260750 A1 | 11/2007 | Feied et al. | |
| 2007/0276697 A1 | 11/2007 | Wiley et al. | |
| 2007/0294765 A1 | 12/2007 | Rihn et al. | |
| 2007/0299915 A1 | 12/2007 | Shraim et al. | |
| 2008/0033750 A1 | 2/2008 | Swiss et al. | |
| 2008/0103836 A1 | 5/2008 | Park et al. | |
| 2008/0112411 A1 | 5/2008 | Stafford et al. | |

(56) References Cited

U.S. PATENT DOCUMENTS

| | | |
|---|---|---|
| 2008/0152107 A1 | 6/2008 | Mendiola |
| 2008/0215361 A1 | 9/2008 | Nunnari et al. |
| 2008/0262948 A1 | 10/2008 | Grady et al. |
| 2009/0030719 A1 | 1/2009 | Nadas et al. |
| 2009/0064330 A1 | 3/2009 | Shraim et al. |
| 2009/0094051 A1 | 4/2009 | Ard et al. |
| 2009/0100099 A1 | 4/2009 | Buckwaiter |
| 2009/0112707 A1 | 4/2009 | Weiss et al. |
| 2009/0204477 A1 | 8/2009 | Urso |
| 2009/0287558 A1 | 11/2009 | Seth et al. |
| 2009/0313112 A1 | 12/2009 | Champ et al. |
| 2009/0327363 A1 | 12/2009 | Cullen et al. |
| 2010/0030667 A1 | 2/2010 | Chudy et al. |
| 2010/0070298 A1 | 3/2010 | Kalies |
| 2010/0144259 A1 | 6/2010 | Allexon et al. |
| 2010/0145730 A1 | 6/2010 | Abreu |
| 2010/0161353 A1 | 6/2010 | Mayaud |
| 2010/0217622 A1 | 8/2010 | Brown et al. |
| 2010/0285821 A1 | 11/2010 | Smeeding et al. |
| 2010/0293236 A1 | 11/2010 | Wisner et al. |
| 2011/0112871 A1 | 5/2011 | Simonowski et al. |
| 2011/0161109 A1 | 6/2011 | Pinsonneault et al. |
| 2011/0196697 A1 | 8/2011 | Akers |
| 2011/0288925 A1 | 11/2011 | Thomas et al. |
| 2012/0053958 A1 | 3/2012 | Marshall et al. |
| 2012/0136809 A1 | 5/2012 | Cannata et al. |
| 2012/0143627 A1 | 6/2012 | Ruben et al. |
| 2012/0166268 A1 | 6/2012 | Griffiths |
| 2012/0179481 A1 | 7/2012 | Patel et al. |
| 2012/0185263 A1 | 7/2012 | Emert |
| 2012/0185264 A1 | 7/2012 | Demogenes et al. |
| 2012/0253829 A1 | 10/2012 | John et al. |
| 2012/0253830 A1 | 10/2012 | John et al. |
| 2012/0253831 A1 | 10/2012 | John et al. |
| 2012/0253832 A1 | 10/2012 | John et al. |
| 2012/0253833 A1 | 10/2012 | John et al. |
| 2012/0253846 A1 | 10/2012 | John et al. |
| 2012/0265591 A1 | 10/2012 | Hwang |
| 2013/0041968 A1 | 2/2013 | Cohen et al. |
| 2013/0103602 A1 | 4/2013 | Melnick et al. |
| 2013/0144715 A1* | 6/2013 | Kranzley ........... G06Q 30/0251 705/14.49 |
| 2013/0197980 A1 | 8/2013 | Lerner et al. |
| 2013/0246082 A1 | 9/2013 | Brylawski et al. |
| 2013/0311389 A1 | 11/2013 | Kaehler et al. |
| 2014/0039911 A1* | 2/2014 | Iyer ................... G06Q 30/0207 705/2 |
| 2014/0088985 A1 | 3/2014 | Grant et al. |
| 2014/0214435 A1 | 7/2014 | Previdi |
| 2014/0249861 A1 | 9/2014 | Gamble et al. |
| 2014/0249864 A1 | 9/2014 | Sultan et al. |
| 2014/0278456 A1 | 9/2014 | Milosevich et al. |
| 2015/0088557 A1 | 3/2015 | Huynh et al. |
| 2015/0142479 A1 | 5/2015 | Porter et al. |
| 2015/0149197 A1 | 5/2015 | Guinan |
| 2015/0154565 A1 | 6/2015 | Kaehler et al. |
| 2015/0154588 A1 | 6/2015 | Purves et al. |
| 2015/0195224 A1 | 7/2015 | Karnin et al. |
| 2015/0213195 A1 | 7/2015 | Blechman |
| 2015/0234991 A1 | 8/2015 | Pinsonneault |
| 2015/0235177 A1 | 8/2015 | Shraim et al. |
| 2015/0269695 A1* | 9/2015 | Pinsonneault ......... G06Q 10/10 705/2 |
| 2015/0332422 A1 | 11/2015 | Gilmartin |
| 2015/0371000 A1 | 12/2015 | Pinsonneault |
| 2016/0012465 A1 | 1/2016 | Sharp |
| 2016/0140593 A1 | 5/2016 | Smeeding et al. |
| 2016/0213512 A1 | 7/2016 | Palanker et al. |
| 2016/0267544 A1 | 9/2016 | Flood et al. |
| 2016/0267545 A1 | 9/2016 | Glass et al. |
| 2016/0307195 A1 | 10/2016 | Cantwell et al. |
| 2016/0358142 A1 | 12/2016 | Hillen |
| 2016/0359795 A1 | 12/2016 | Fehling |
| 2017/0034087 A1 | 2/2017 | Borenstein et al. |
| 2017/0220768 A1 | 8/2017 | Tanner, Jr. et al. |
| 2017/0323295 A1* | 11/2017 | Kranzley ........... G06Q 30/0611 |
| 2017/0324695 A1 | 11/2017 | Fischer et al. |
| 2018/0012244 A1* | 1/2018 | Leonardi ............. G06Q 10/087 |
| 2018/0366810 A1 | 12/2018 | Nero et al. |
| 2019/0213212 A1 | 7/2019 | Adato et al. |
| 2019/0385733 A1 | 12/2019 | Kaye et al. |
| 2019/0385734 A1 | 12/2019 | Pinsonneault |
| 2021/0319887 A1 | 10/2021 | Derrick, Jr. et al. |

FOREIGN PATENT DOCUMENTS

| | | |
|---|---|---|
| CA | 2792252 A1 | 4/2013 |
| CA | 2810686 A1 | 10/2013 |
| CN | 102362778 | 2/2012 |
| KR | 100755440 | 9/2007 |
| KR | 100793852 | 1/2008 |
| KR | 101038074 | 6/2011 |
| KR | 101101692 | 12/2011 |
| KR | 20110138108 | 12/2011 |
| KR | 20110138572 | 12/2011 |
| KR | 101154858 | 6/2012 |
| WO | WO 1991/006917 A1 | 5/1991 |
| WO | WO 1995/003569 A2 | 2/1995 |
| WO | WO 1997/025682 A1 | 7/1997 |
| WO | WO 1998/050871 A1 | 11/1998 |
| WO | WO 2000/039737 A1 | 7/2000 |
| WO | WO 2003/098401 A2 | 11/2003 |
| WO | WO 2007/025295 A2 | 3/2007 |
| WO | WO 2007/094772 A1 | 8/2007 |
| WO | WO 2008/092109 A2 | 7/2008 |

OTHER PUBLICATIONS

United States Patent and Trademark Office, Non-Final Office Action received for U.S. Appl. No. 16/867,286, dated Feb. 22, 2022, 38 pages, U.S.

United States Patent and Trademark Office, Notice of Allowance received for U.S. Appl. No. 17/219,526, dated Feb. 3, 2022, 48 pages, U.S.

Zhu, V. et al., "Data for drugs available through low-cost prescription drug programs are available through pharmacy benefit manager and claims data," BMC Clinical Pharmacology, Jun. 22, 2012, vol. 12, No. 12., BioMed Central Ltd., UK.

Scientific and Technical Information Center, Report of Information from Dialog (NPL (non-patent literature) Search Results, Abstracts only), dated Nov. 1, 2021, (Year: 2021), 9 pages.

United States Patent and Trademark Office, Advisory Action received for Application No. 16/45 3,5 09, dated Oct. 12, 2021, 5 pages, U.S.

United States Patent and Trademark Office, Final Office Action received for U.S. Appl. No. 16/551,962, dated Nov. 4, 2021, 32 pages, U.S.

United States Patent and Trademark Office, Final Office Action received for U.S. Appl. No. 16/832,318, dated Nov. 3, 2021, 22 pages, U.S.

Google NPL (non-patent literature) Search on "pharmacy payment benefit copay NDC database", retrieved from the Internet at <https//scholar.google.com/scholar?hl=en&as_sdt-3,47&g=pharmacy+payment+benefit+copay+NDC+database> on Feb. 20, 2022 at 3:02 pm, 1 page.

Google NPL (non-patent literature) Search on "pharmacy payment benefit copay NDC database", retrieved from the Internet at <https://www.google.com/search?g=pharmacy+payment+benefit+copay+ndc+database&source=int&tbs=cdr%3A1%2Ccd_min%3A1%2F1%2F2010%2 . . . > on Feb. 20, 2022 at 3:00 pm, 2 pages.

United States Patent and Trademark Office, Advisory Action received for U.S. Appl. No. 16/792,413, dated Mar. 10, 2022, 4 pages, US.

United States Patent and Trademark Office, Notice of Allowance and Fee(s) Due received for U.S. Appl. No. 17/219,526, dated Mar. 22, 2022, 11 pages, US.

United States Patent and Trademark Office, Notice of Allowance and Fee(s) Due received for U.S. Appl. No. 16/551,962, dated Mar. 16, 2022, 10 pages, US.

United States Patent and Trademark Office, Notice of Allowance and Fee(s) Due received for U.S. Appl. No. 17/092,705, dated Mar. 24, 2022, 9 pages, US.

(56) References Cited

OTHER PUBLICATIONS

United States Patent and Trademark Office, Notice of Allowance and Fee(s) Due received for U.S. Appl. No. 16/551,962, dated Mar. 1, 2022, 14 pages, US.
United States Patent and Trademark Office, Notice of Allowance received for U.S. Appl. No. 16/043,401, dated Aug. 10, 2020, 9 pages, U.S.A.
U.S. Appl. No. 16/792,413, "Method, Apparatus and Computer Program Product for Partitioning Prescription Transaction Costs in an Electronic Prescription Transaction," Unpublished (filed Feb. 17, 2020), (Jared Burdine, Inventor) (McKesson Corporation, Assignee).
U.S. Appl. No. 16/867,286, "Method, Apparatus, and Computer Program Product for Constructing Electronic Message Responses Dependent Upon Historical Information," Unpublished (filed May 5, 2020), (Jared Burdine, et al., Inventor) (McKesson Corporation, Assignee).
U.S. Appl. No. 16/043,401, "Computing System and Method for Automatically Reversing an Action Indicated by an Electronic Message," Unpublished (filing date Jul. 24, 2018), (Patrick Harris, Inventors) (McKesson Corporation, Assignee).
Pharmacy Reject Codes NCPDP, 5 pages.
St. Vincent's first to use Birmingham startup's information system. The Birmingham News [Online] Apr. 11, 2005. URL: http://www.awarix.com.
St. Vincent's is Digital Flagship D. Lockridge; Birmingham Medical News [Online] Sep. 2005.
Two automatic identification technology, neither new in the sense if being recent developments . . . . Patient Safety & Quality Healthcare [Online] August 2005_ URL: http://www_awarix.com.
Advisory Action for U.S. Appl. No. 14/193,294 dated Nov. 9, 2017, 3 pages.
Advisory Action for U.S. Appl. No. 15/085,166 dated Apr. 11, 2019, 4 pages.
Advisory Action for U.S. Appl. No. 15/085,166 dated Apr. 29, 2020, 3 pages.
Advisory Action for U.S. Appl. No. 15/137,371 dated Feb. 25, 2019, 5 pages.
Advisory Action for U.S. Appl. No. 15/427,746 dated Jul. 2, 2019, 2 pages.
Advisory Action received for U.S. Appl. No. 15/085,166, dated Jan. 29, 2021, 3 pages, US.
Almaro, Moshe; "Recovery and Reuse of Unused Prescription Drugs" MIT What Matters: Aug. 2005.
American Society of Health-System Pharmacists (ASHP), "Is Prescribing the Next Step in the Evolution of Pharmacy?" May 15, 2012.
Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.
Anonymous, Medic; On-line Goes In-House, Chain Store Age Executive, Jan. 1987, vol. 63, Issue 1, USA; Abstract only.
Anonymous, Pharmacy Industry Leaders Launch Firm to Supply Real-Time Data, PR Newswire, Jul. 30, 2001, p. 1, New York, NY, USA.
Anonymous, TechRx Announces Successful Beta Deployment of T-Rex. PR Newswire. May 13, 2002.
Consalvo, Bob; "City of Boston in the City Council" hearing notice, Dec. 6, 2006.
Coping with Information Overload. The News Source for Healthcare Information Technology [Online] Nov. 2004. URL: http://www.awarix.com.
Decision to Grant European Patent Application No. 13809457.8 dated May 18, 2017.
Examiner's Answer for U.S. Appl. No. 14/145,027 dated Sep. 7, 2016, 27 pages.
Extended European Search Report for European Application No. 13809457.8 dated Apr. 15, 2016, 6 pages.

Final Office Action for U.S. Appl. No. 12/140,015 dated Jan. 31, 2011, 10 pages.
Final Office Action for U.S. Appl. No. 12/415,062 dated Oct. 6, 2011, 18 pages.
Final Office Action for U.S. Appl. No. 12/555,589 dated Apr. 11, 2012, 17 pages.
Final Office Action for U.S. Appl. No. 12/560,071 dated Aug. 28, 2015, 8 pages.
Final Office Action for U.S. Appl. No. 12/560,071 dated Nov. 8, 2012, 11 pages.
Final Office Action for U.S. Appl. No. 12/570,982 dated Apr. 11, 2014, 22 pages.
Final Office Action for U.S. Appl. No. 12/570,982 dated Aug. 28, 2015, 10 pages.
Final Office Action for U.S. Appl. No. 12/570,982 dated Jan. 17, 2013, 19 pages.
Final Office Action for U.S. Appl. No. 12/730,015 dated Aug. 14, 2012, 10 pages.
Final Office Action for U.S. Appl. No. 12/978,898 dated May 16, 2013, 16 pages.
Final Office Action for U.S. Appl. No. 13/721,890 dated Jun. 24, 2015, 14 pages.
Final Office Action for U.S. Appl. No. 13/721,890 dated Nov. 25, 2016, 12 pages.
Final Office Action for U.S. Appl. No. 13/782,909 dated May 31, 2016, 18 pages.
Final Office Action for U.S. Appl. No. 13/782,909 dated Oct. 6, 2015, 24 pages.
Final Office Action for U.S. Appl. No. 13/804,175 dated Oct. 6, 2015, 6 pages.
Final Office Action for U.S. Appl. No. 13/827,676 dated Jul. 13, 2015, 17 pages.
Final Office Action for U.S. Appl. No. 14/090,113 dated Jan. 6, 2016, 18 pages.
Final Office Action for U.S. Appl. No. 14/090,122 dated Apr. 22, 2016, 13 pages.
Final Office Action for U.S. Appl. No. 14/145,027 dated Nov. 19, 2015, 12 pages.
Final Office Action for U.S. Appl. No. 14/193,294 dated May 2, 2016, 29 pages.
Final Office Action for U.S. Appl. No. 14/218,326 dated Jun. 30, 2016, 17 pages.
Final Office Action for U.S. Appl. No. 15/085,166, dated Dec. 4, 2020, 11 pages.
Final Office Action for U.S. Appl. No. 15/137,371 dated Nov. 28, 2018, 24 pages.
Final Office Action for U.S. Appl. No. 15/427,746 dated Apr. 15, 2019, 9 pages.
Kaplan et al., "Let the Needles Do the Talking! Evaluating the New Haven Needle Exchange." Interfaces 23:1, Jan.-Feb. 1993 (pp. 7-26).
Lamb, J., New Era of Electronic Medicine Management: E-Prescriptions, Britain's Traditionally Cautious National Health Service is Starting Trials for Online Prescription, with the Aim of Cutting Costs, Finance Times, London, Feb. 21, 2001, p. 6, London, United Kingdom.
Letter Restarting Period for Response for U.S. Appl. No. 13/721,890 dated Jan. 14, 2015, 11 pages.
Marie Chisholm et al. "Pharmaceutical Manufacturer Assistance Program." Arch Intern Med. vol. 162, Apr. 8, 2002.
Non-Final Office Action for U.S. Appl. No. 12/560,071 dated Jun. 21, 2012, 11 pages.
Non-Final Office Action for U.S. Appl. No. 12/570,982 dated Jun. 20, 2012, 10 pages.
Non-Final Office Action for U.S. Appl. No. 14/193,294 dated Feb. 21, 2017, 32 pages.
Non-Final Office Action for U.S. Appl. No. 15/085,166 dated Jun. 12, 2020, 26 pages.
Non-Final Office Action for U.S. Appl. No. 16/180,915 dated Jun. 1, 2020, 40 pages.
Non-final Office Action for U.S. Appl. No. 12/140,015 dated Oct. 8, 2010, 9 pages.

(56) References Cited

OTHER PUBLICATIONS

Non-final Office Action for U.S. Appl. No. 12/189,650 dated Jan. 22, 2010, 11 pages.
Non-final Office Action for U.S. Appl. No. 12/189,654 dated Jan. 22, 2010, 11 pages.
Non-Final Office Action for U.S. Appl. No. 12/388,956 dated Feb. 3, 2011, 11 pages.
Non-Final Office Action for U.S. Appl. No. 12/415,062 dated Mar. 30, 2011, 23 pages.
Non-Final Office Action for U.S. Appl. No. 12/555,589 dated Dec. 9, 2011, 12 pages.
Non-Final Office Action for U.S. Appl. No. 12/560,071 dated Sep. 23, 2014, 17 pages.
Non-Final Office Action for U.S. Appl. No. 12/570,982 dated Sep. 12, 2013, 22 pages.
Non-Final Office Action for U.S. Appl. No. 12/730,015 dated Mar. 6, 2012, 9 pages.
Non-Final Office Action for U.S. Appl. No. 12/956,411 dated Jan. 24, 2011, 9 pages.
Non-Final Office Action for U.S. Appl. No. 12/978,898 dated Feb. 6, 2013, 12 pages.
Non-Final Office Action for U.S. Appl. No. 12/982,395 dated Dec. 11, 2012, 13 pages.
Non-Final Office Action for U.S. Appl. No. 13/721,890 dated Jan. 9, 2015, 11 pages.
Non-Final Office Action for U.S. Appl. No. 13/721,890 dated Jun. 14, 2016, 9 pages.
Non-final Office Action for U.S. Appl. No. 13/782,909 dated Feb. 11, 2016, 17 pages.
Non-Final Office Action for U.S. Appl. No. 13/827,676 dated Dec. 26, 2014, 13 pages.
Non-final Office Action for U.S. Appl. No. 13/827,676 dated Dec. 30, 2015, 23 pages.
Non-Final Office Action for U.S. Appl. No. 14/145,027 dated Mar. 23, 2015, 13 pages.
Non-Final Office Action for U.S. Appl. No. 15/137,371 dated May 29, 2018, 19 pages.
Non-Final Office Action for U.S. Appl. No. 15/427,746 dated Oct. 18, 2018, 9 pages.
Non-Final Office Action for U.S. Appl. No. 16/819,258 dated Sep. 4, 2020, 6 pages.
Non-Final Office Action received for U.S. Appl. No. 15/085,166, dated Mar. 17, 2021, 11 pages.
Non-Final Office Action received for U.S. Appl. No. 16/551,962, dated Mar. 2, 2021, 16 pages.
Non-Final Office Action received for U.S. Appl. No. 16/453,509 dated Mar. 26, 2021, 45 pages.
Non-Final Office Action received for U.S. Appl. No. 16/832,318 dated Apr. 23, 2021, 52 pages.
Notice of Allowance and Fees(s) Due for U.S. Appl. No. 15/925,011 dated Jan. 22, 2021, 15 pages.
Notice of Allowance for U.S. Appl. No. 16/180,915 dated Dec. 11, 2020, 23 pages.
Notice of Allowance for U.S. Appl. No. 11/674,069 dated Jul. 19, 2010, 13 pages.
Notice of Allowance for U.S. Appl. No. 12/140,015 dated Jun. 10, 2011, 10 pages.
Notice of Allowance for U.S. Appl. No. 12/165,221 dated Nov. 16, 2010, 6 pages.
Notice of Allowance for U.S. Appl. No. 12/189,650 dated Aug. 13, 2010, 11 pages.
Notice of Allowance for U.S. Appl. No. 12/388,956 dated Jun. 14, 2011, 9 pages.
Notice of Allowance for U.S. Appl. No. 12/956,411 dated Aug. 5, 2011, 8 pages.
Notice of Allowance for U.S. Appl. No. 12/982,395 dated Apr. 24, 2013, 9 pages.
Notice of Allowance for U.S. Appl. No. 14/181,011 dated May 15, 2019, 9 pages.
Notice of Allowance for U.S. Appl. No. 15/137,371 dated May 2, 2019, 11 pages.
Notice of Allowance for U.S. Appl. No. 15/427,746 dated Dec. 4, 2019, 5 pages.
Notice of Allowance for U.S. Appl. No. 15/427,746 dated Jul. 31, 2019, 8 pages.
Notice of Allowance received for U.S. Appl. No. 14/643,468, dated Oct. 24, 2018, 22 pages.
Notice of Allowance received for U.S. Appl. No. 14/181,011, filed Feb. 13, 2019, 9 pages.
Office Action for U.S. Appl. No. 14/193,294 dated Aug. 4, 2017, 31 pages.
Office Action for U.S. Appl. No. 14/193,294 dated Mar. 22, 2018, 28 pages.
Office Action for U.S. Appl. No. 14/193,294 dated Sep. 19, 2018, 27 pages.
Office Action for U.S. Appl. No. 14/229,043 dated Feb. 27, 2019, 18 pages.
Office Action for U.S. Appl. No. 14/229,043 dated Jul. 24, 2017, 19 pages.
Office Action for U.S. Appl. No. 14/229,043 dated Sep. 5, 2019, 22 pages.
Office Action for U.S. Appl. No. 14/229,043 dated Sep. 14, 2018, 17 pages.
Office Action for U.S. Appl. No. 14/643,468 dated Mar. 8, 2018, 11 pages.
Office Action for U.S. Appl. No. 15/085,166 dated Dec. 27, 2018, 24 pages.
Office Action for U.S. Appl. No. 15/085,166 dated Jun. 29, 2018, 19 pages.
Office Action for U.S. Appl. No. 15/085,166 dated Mar. 3, 2020, 25 pages.
Office Action for U.S. Appl. No. 15/085,166 dated Sep. 4, 2019, 23 pages.
Office Action for U.S. Appl. No. 15/422,184 dated Aug. 27, 2019, 16 pages.
Office Action for U.S. Appl. No. 15/422,184 dated Feb. 15, 2019, 15 pages.
Office Action for U.S. Appl. No. 15/422,184 dated Jan. 14, 2020, 19 pages.
Office Action for U.S. Appl. No. 15/422,184 dated Sep. 10, 2018, 13 pages.
Office Action for U.S. Appl. No. 15/925,011 dated Jun. 27, 2019, 15 pages.
Office Action for U.S. Appl. No. 15/925,011 dated Oct. 24, 2019, 19 pages.
Office Action for U.S. Appl. No. 15/925,948 dated Jun. 25, 2019, 13 pages.
Office Action for U.S. Appl. No. 15/925,948 dated Oct. 23, 2019, 18 pages.
Office Action for U.S. Appl. No. 12/570,982 dated Apr. 8, 2015, 9 pages.
Office Action for U.S. Appl. No. 13/782,909 dated Jun. 25, 2015, 16 pages.
Office Action for U.S. Appl. No. 13/804,175 dated Mar. 13, 2015, 9 pages.
Office Action for U.S. Appl. No. 14/090,113 dated Jun. 18, 2015, 14 pages.
Office Action for U.S. Appl. No. 14/090,122 dated Oct. 21, 2016, 12 pages.
Office Action for U.S. Appl. No. 14/090,122 dated Sep. 11, 2015, 10 pages.
Office Action for U.S. Appl. No. 14/181,011 dated Feb. 29, 2016, 23 pages.
Office Action for U.S. Appl. No. 14/181,011 dated Mar. 20, 2017, 28 pages.
Office Action for U.S. Appl. No. 14/181,011 dated Oct. 20, 2016, 28 pages.
Office Action for U.S. Appl. No. 14/181,011 dated Sep. 12, 2017, 17 pages.
Office Action for U.S. Appl. No. 14/193,294 dated Dec. 17, 2015, 21 pages.

(56) References Cited

OTHER PUBLICATIONS

Office Action for U.S. Appl. No. 14/218,326 dated Dec. 1, 2015, 13 pages.
Opar, Alisa; "Rising drug costs prompt new uses for old pills." Nature Medicine, 1211333 (2006).
PTAB Decision on Appeal for U.S. Appl. No. 14/145,027 dated May 31, 2018, 11 pages.
PTAB Decision on Request for Rehearing for U.S. Appl. No. 14/145,027 dated Aug. 30, 2018, 9 pages.
Sampson, R.J., Taking Control of Health Care Costs, Best's Review—Life Health Insurance Edition, Nov. 1983, vol. 84, Issue 7, USA; Abstract only.
Siler, Sharon et al., "Safe Disposal of Unused Controlled Substances" Avalere Health 2008.
Strom, Stephanie; "Old Pills Finding New Medicine Cabinets" NY Times, May 18, 2005.
Subnotebooks, Phones, and More. St. Vincent's Gets on Track. Mobile Health Data [Online], Nov. 19, 2004. URL:http://www.awarix.com.
Supplemental Notice of Allowability received for U.S. Appl. No. 16/180,915, dated Jan. 28, 2021, 2 pages.
Supplemental Notice of Allowability received for U.S. Appl. No. 16/180,915, dated Mar. 12, 2021, 10 pages.
U.S. Notice of Allowance received for U.S. Appl. No. 16/819,258, dated Nov. 16, 2020, 8 pages, U.S.
U.S. Appl. No. 14/229,043, "Systems And Methods For Monitoring And Reporting Redemption Information At A Pharmacy For Patient Incentive Information Identified At The Time Of Prescribing," Unpublished (filed Mar. 28, 2014), (Roger Pinsonneault, Inventor), (McKesson Corporation, Assignee), abandoned.
U.S. Appl. No. 15/084,034, "Prescription Provider System," Unpublished (filed Mar. 29, 2016), (Scott Genone, Inventor), (McKesson Corporation, Assignee), abandoned.
U.S. Appl. No. 15/085,166, "Alternative Therapy Identification System", Unpublished (filed Mar. 30, 2016), (Elizabeth Kaye, Inventor), (McKesson Corporation, Assignee), pending.
U.S. Appl. No. 17/092,705, "Computing System and Method for Automatically Reversing an Action Indicated by an Electronic Message," Unpublished (filing date Nov. 9, 2020), (Patrick Harris, Inventor) (McKesson Corporation, Assignee), pending.
U.S. Appl. No. 16/832,318, "Method, Apparatus, And Computer Program Product for Estimated Prescription Costs", Unpublished (filed Mar. 27, 2020), (Stacy Hopkins, Inventor), (McKesson Corporation, Assignee), pending.
United States Patent and Trademark Office, Advisory Action for U.S. Appl. No. 15/422,184, filed Jun. 25, 2019, 4 pages, U.S.A.
United States Patent and Trademark Office, Advisory Action for U.S. Appl. No. 15/422,184, filed Mar. 26, 2020, 5 pages, U.S.A.
United States Patent and Trademark Office, Advisory Action for U.S. Appl. No. 15/925,011, filed Jan. 31, 2020, 3 pages, U.S.A.
United States Patent and Trademark Office, Advisory Action for U.S. Appl. No. 15/925,948, filed Jan. 31, 2020, 4 pages, U.S.A.
United States Patent and Trademark Office, Notice of Allowability received for U.S. Appl. No. 15/422,184, filed Nov. 16, 2020, 2 pages, U.S.A.
United States Patent and Trademark Office, Notice of Allowance received for U.S. Appl. No. 15/422,184, filed Oct. 13, 2020, 12 pages, U.S.A.
United States Patent and Trademark Office, Notice of Allowance received for U.S. Appl. No. 15/925,948, filed Nov. 5, 2020, 22 pages, U.S.A.
United States Patent and Trademark Office, Office Action for U.S. Appl. No. 15/925,011, filed Apr. 8, 2020, 17 pages, U.S.A.
United States Patent and Trademark Office, Office Action for U.S. Appl. No. 15/925,948, filed Mar. 23, 2020, 29 pages, U.S.A.
United States Patent and Trademark Office, Office Action received for U.S. Appl. No. 15/422,184, filed May 18, 2020, 31 pages, U.S.A.
United States Patent and Trademark Office, Office Action received for U.S. Appl. No. 15/925,011, filed Oct. 8, 2020, 8 pages, U.S.A.

Wisconsin Physicians Service (WPS) Insurance Corporation, "How to Read Your Explanation of Benefits Chart," Jun. 16, 2012.
www.ncoil.org/news/DrugCards2.doc dated Apr. 2002, 5 pages.
United States Patent and Trademark Office, Notice of Allowance received for U.S. Appl. No. 17/092,705, dated Dec. 23, 2021, 42 pages, U.S.
United States Patent and Trademark Office, Non-Final Office Action received for U.S. Appl. No. 15/085,166, dated Jan. 10, 2022, 12 pages, U.S.
United States Patent and Trademark Office, Final Office Action received for U.S. Appl. No. 16/792,413, dated Jan. 10, 2022, 80 pages, U.S.
United States Patent and Trademark Office, Non-Final Office Action received for U.S. Appl. No. 16/453,509, dated Apr. 28, 2022, 16 pages, U.S.A.
United States Patent and Trademark Office, Non-Final Office Action received for U.S. Appl. No. 16/552,021, dated May 3, 2022, 60 pages, U.S.A.
United States Patent and Trademark Office, Non-Final Office Action received for U.S. Appl. No. 17/175,939, dated May 12, 2022, 48 pages, U.S.A.
CMS Updates Drug Dashboards with Prescription Drug Pricing and Spending Data, Data, Medicare Part D, Prescription drugs (Mar. 14, 2019).
How to Estimate the Cost of a Prescription. Pam Olson, Sr. Client Services Executive, Navitus Health Solutions (Year: 2015).
United States Patent and Trademark Office, Final Office Action received for U.S. Appl. No. 16/453,509, dated Aug. 18, 2021, 16 pages, U.S.
United States Patent and Trademark Office, Non-Final Office Action received for U.S. Appl. No. 16/792,413, dated Aug. 5, 2021, 32 pages, U.S.
United States Patent and Trademark Office, Notice of Allowance received for U.S. Appl. No. 15/085,166, dated Sep. 10, 2021, 21 pages, U.S.
United States Patent and Trademark Office, Corrected Notice of Allowability received for U.S. Appl. No. 15/085,166, dated Sep. 20, 2021, 6 pages, U.S.
Chu, Kuan-Yu, et al., "Incremental analysis of the reengineering of an outpatient billing process: an empirical study in a public hospital", BMC Health Services Research, Jun. 13, 2013, vol. 13, No. 215, 8 pages, BioMed Central Ltd, UK.
Google Patents Search (including Web Search History, Prior Art Search Printable History Generator) on "pharmacy payment benefit copay NDC database) (prescription) (code) (refills) (error code) country:US before Filing: Dec. 31, 2013", retrieved from the Internet at <https://patents.google.com/?q=pharmacy+payment+benefit+copay+ NDC+database&q=prescription&q=code&q=refills&q=error+code&country=US&before-filing:Dec. 31, 2013> retrieved on Jun. 1, 2022, 4 pages.
Google Scholar Search (including Web Search History, Prior Art Search Printable History Generator) on "pharmacy payment benefit copay NDC database prescription . . . ", retrieved from the Internet at <https://scholar.google.com/scholar?hl=en&as_sdt-0%2C47&as_ylo-2010&as_yhi–2013&q=pharmacy+payment+benefit+copay+NDC+database+pres . . . > retrieved on Jun. 1, 2022, 3 pages.
United States Patent and Trademark Office, Non-Final Office Action received for U.S. Appl. No. 16/792,413, dated May 24, 2022, 48 pages, US.
United States Patent and Trademark Office, Non-Final Office Action received for U.S. Appl. No. 17/144,426, dated May 31, 2022, 42 pages, US.
United States Patent and Trademark Office, Non-Final Office Action received for U.S. Appl. No. 16/832,318, dated Jun. 8, 2022, 17 pages, US.
United States Patent and Trademark Office, Notice of Allowance received for U.S. Appl. No. 17/092,705, dated May 31, 2022, 9 pages, US.
United States Patent and Trademark Office, Notice of Allowance received for U.S. Appl. No. 17/219,526, dated Jun. 2, 2022, 8 pages, US.

(56) References Cited

OTHER PUBLICATIONS

United States Patent and Trademark Office, Notice of Allowance received for U.S. Appl. No. 16/551,962, dated Jun. 8, 2022, 11 pages, US.

United States Patent and Trademark Office, Notice of Allowance received for U.S. Appl. No. 15/085,166, dated Jun. 15, 2022, 18 pages, U.S.

Dubois, Robert W., "Rx Drug Costs: List Prices Versus Net Prices And The Importance Of Staying Within The Data", Health Affairs Blog, Mar. 2019, 7 pages.

Kamal, Rabah, et al., "What are the recent and forecasted trends in prescription drug spending?" Peterson-KFF Health System Tracker, Feb. 20, 2019, 19 pages, Peterson Center on Healthcare.

Cepeda, Maria Soledad, et al., "Quantification of missing prescriptions in commercial claims databases : results of a cohort study.", Pharmacoepidemiology and Drug Safety, Apr. 2017, pp. 386-392, vol. 26, Epub Jan. 25, 2017 on Wiley Online Library.

United States Patent and Trademark Office, Final Office Action received for U.S. Appl. No. 16/867,286, dated Sep. 8, 2022, 19 pages, U.S.

United States Patent and Trademark Office, Notice of Allowance received for U.S. Appl. No. 16/792,413, dated Sep. 8, 2022, 18 pages, U.S.

United States Patent and Trademark Office, Notice of Allowance received for U.S. Appl. No. 16/453,509, dated Oct. 3, 2022, 23 pages, U.S.

United States Patent and Trademark Office, Final Office Action received for U.S. Appl. No. 17/175,939, dated Oct. 5, 2022, 30 pages, U.S.

United States Patent and Trademark Office, Nonfinal Office Action received for U.S. Appl. No. 17/162,461, dated Oct. 5, 2022, 47 pages, U.S.

United States Patent and Trademark Office, Nonfinal Office Action received for Application No. 17/15 8,118, dated Oct. 7, 2022, 46 pages, U.S.

United States Patent and Trademark Office, Notice of Allowance received for U.S. Appl. No. 16/552,021, dated Oct. 20, 2022, 14 pages, U.S.

American Hospital Association, "Drug Price Proposals", dated Apr. 2019, retrieved from the Internet at <URL: https://www.aha.org/system/files/media/file/2019/04/aha-drug-policy-recommendations_2.pdf>, 8 pages.

California Health Care Foundation, "When the Price Is Not Right: State Options on Prescription Drug Pricing", dated Jun. 2016, retrieved from the Internet at: <URL: https://www.chef.org/wp-content/uploads/2017/12/PDF-WhenStateRxPricing.pdf>, 16 pages.

Hsee, Christopher K., et al., "General Evaluability Theory", Perspectives on Psychological Science, Jul. 2010, pp. 343-355, vol. 5, No. 4, Sage Publications, Inc. on behalf of the Association for Psychological Science retrieved from the Internet at <URL: https://www.jstor.org/stable/41613442>.

United States Patent and Trademark Office, Advisory Action received for U.S. Appl. No. 16/867,286, dated Dec. 6, 2022, 8 pages, U.S.

United States Patent and Trademark Office, Final Office Action received for U.S. Appl. No. 17/144,426, dated Dec. 8, 2022, 21 pages, U.S.

United States Patent and Trademark Office, Notice of Allowance received for U.S. Appl. No. 16/832,318, dated Dec. 8, 2022, 26 pages, U.S.

Van Nuys, Ph.D., Karen, et al., "Prescription Drug Copayment Coupon Landscape", Drug Pricing White Paper, USC Leonard D. Schaeffer Center for Health Policy and Economics, Feb. 7, 2018, retriebed from the Internet at <URL: https://healthpolicy.usc.edu/research/prescription-drug-copayment-coupon-landscape/> 21 pages.

* cited by examiner

METHOD, APPARATUS, AND COMPUTER PROGRAM PRODUCT FOR PERFORMING AN ALTERNATIVE EVALUATION PROCEDURE IN RESPONSE TO AN ELECTRONIC MESSAGE

TECHNOLOGICAL FIELD

Embodiments of the present invention relate generally to electronic messages, and more particularly, to methods, apparatuses, and computer program products for performing an alternative evaluation procedure in response to an electronic message.

BACKGROUND

Electronic messages are frequently originated, then transmitted and routed according to an evaluation system identified by the message. A processing system may therefore route the message to the indicated evaluation system, await a response, and forward or route the response message to the message originator or requestor. However, in some examples, the original electronic message does not include the information needed to obtain the best response or most accurate response to the message, nor does the message originator have the ability to determine which evaluation system may provide the best response or most accurate response to the message.

BRIEF SUMMARY

Methods, apparatuses, and computer program products are therefore provided for performing an alternative evaluation procedure in response to an electronic message. The alternative evaluation procedure may further result in modifying the indicated evaluation system in the message.

Requesting computers may generate and transmit messages to a service provider computer that in turn routes the message to an evaluation system for evaluation and return of a response to the service provider computer. The message indicates the evaluation system to which the request should be forwarded. The service provider handles processing and routing of such messages, and reconciliation of responses so that a corresponding response provided by the evaluation system is returned to the requesting computer. At various stages of the processing and editing, the service provider computer may perform additional edits or manipulations of such messages and responses.

According to certain example embodiments provided herein, the service provider computer may therefore utilize historical data, such as prior transactions transmitted amongst various requesting computers and/or evaluation systems, to edit such messages and/or responses. Additionally, or alternatively, the service provider computer may receive and store eligibility data provided by evaluation computers. The historical data and/or eligibility data may enable the service provider to predict, or provide more accurate predictions, of information returned by evaluation computers. Accordingly, the service provider computer may edit, initiate edits, or recommend edits to a message based on the historical data and/or evaluation data in order to obtain improved information for the requesting computer.

According to certain embodiments provided herein, a patient may visit a pharmacy to obtain a prescription drug, such as one prescribed in a handwritten prescription, or one electronically submitted to the pharmacy by a prescriber. The patient may provide benefits information to the pharmacy to be processed when obtaining the prescription such that the pharmacy submits a request for the prescription transaction to be processed with the benefits information. However, in some instances, no benefit information may be provided, or the patient may provide benefit information indicating a cash discount system, despite having access to a benefit plan and/or funded benefit plan (described in further detail below). Some patients may provide a cash card associated with a cash discount system, because they have obtained the same prescription in the past, and have done so at a lower out-of-pocket cost via the cash discount system, in comparison to providing their benefit plan information and/or funded benefit plan information. Still further, in certain embodiments, a patient may provide benefit plan information, but not funded benefit plan information, as they may unaware of the availability of the funded benefit plan.

Cash discount systems may provide websites or mobile applications relating to prescription drug prices and offer coupons or discounts on certain prescription medications. A patient may access the website or mobile application to check the cash price of a certain medication while taking into consideration any available discounts or coupons. The cash price is considered the amount paid without submitting a prescription claim to a pharmacy benefits manager (PBM) or other health insurance plan. Certain cash discount systems have no requirements or minimum thresholds for enrollment, and may be open to any customer or patient wanting to enroll.

As referenced herein, a "benefit plan" may include an insurance plan or other pharmacy benefit plan, such as one managed by a pharmacy benefits manager (PBM). A patient may be enrolled in a benefit plan through the patient's employer, other group enrollment opportunities, a private marketplace, and/or the like. A patient may pay insurance premiums to enroll in the plan (e.g., through the patient's employer and/or via a private marketplace).

A "funded benefit plan," may include a particular type of cash discount system designed to enable the purchase of certain prescription drugs at contract rates negotiated between a pharmacy and a benefit plan (e.g., PBM). Members enrolled in a particular benefit plan offered by a PBM that participates in a funded benefit plan, or sponsors a funded benefit plan, may therefore also qualify for benefits under the funded benefit plan, when purchasing certain prescription drugs from contracted pharmacists. In this regard, the funded benefit plan may be referred to as an "extended benefit plan." In some instances a member card showing enrollment in the funded benefit plan may be provided, however, a patient may not necessarily present the card when obtaining a prescription. Certain PBMs may have arrangements established such that every member in the benefit plan is also a member in the funded benefit plan. According to certain embodiments, a funded benefit plan is not considered insurance. Rather, the funded benefit plan is sponsored by the PBM (and/or pharmacy) such that certain prescriptions can be purchased at the pharmacy at the contract rate. In some instances, a funded benefit plan may be established to enable the PBM to compete with other cash discount systems, and to enable the PBM to obtain insight to a greater number of prescription transactions that otherwise may have been processed by and/or transmitted via alternative or competing cash discount systems.

In some instances, an out-of-pocket cost for a particular prescription drug obtainable by a patient via a cash discount system may be lower than an out-of-pocket cost obtainable via a benefit plan be due to the patient being in a deductible phase and not having yet met the deductible required by their funded benefit plan. In such instances, the patient may be accustomed to obtaining the prescription via the cash discount system, and may present the cash card, or indicate to select the cash discount system, when obtaining the prescription at the pharmacy. When patients choose to purchase prescriptions via a cash discount system and not via a benefit plan or funded benefit plan, without the advantages of the example embodiments provided herein, a service provider computer may process and route a prescription transaction to the cash discount system selected by the patient, and the PBM may not become aware of the prescription transaction. A PBM may therefore lose insight to the patient's adherence to prescribed medication. Still further, the patient may be unaware of the funded benefit plan through which the patient may actually obtain the prescription for a lower or equal out-of-pocket cost in comparison to the out-of-pocket cost obtainable via the cash discount system.

As such, according to example embodiments provided herein, a service provider computer may access historical data to determine or predict a funded benefit plan in which the patient is eligible, even if no identifying information associated with the benefit plan and/or funded benefit plan is provided by the patient. Prior prescriptions submitted on behalf of the patient (such as a prescription for a different medication) may indicate benefit plan information. Additionally or alternatively, a payer or PBM associated with the benefit plan may provide eligibility data to the service provider, indicating identifying information of the patient eligible under the funded benefit plan. In this regard, according to certain embodiments provided herein, when a prescription transaction is submitted by a pharmacy computer to a service provider, but does not indicate the funded benefit plan, the service provider may provide feedback to the pharmacy to indicate the patient may be eligible under the funded benefit plan, optionally indicate the price for the prescription drug obtainable via the funded benefit plan, and suggest to a pharmacist to re-enter the prescription transaction to indicate the funded benefit plan.

An apparatus is provided, including at least one processor and at least one memory including computer program code, the at least one memory and the computer program code configured to, with the processor, cause the apparatus to at least parse a message received from a requesting computer to identify an indication of a transaction, an entity identifier, and an identifier of a first evaluation system. The at least one memory and the computer program code are further configured to, with the processor, cause the apparatus to evaluate the entity identifier based on at least one of historical data or eligibility data to determine an alternative evaluation procedure. In certain embodiments, the at least one memory and the computer program code are further configured to, with the processor, cause the apparatus to perform the alternative evaluation procedure to obtain response information regarding the transaction. In certain embodiments, the at least one memory and the computer program code are configured to, with the processor, cause the apparatus to construct a response to the message comprising the response information. The at least one memory and the computer program code are further configured to, with the processor, cause the apparatus to transmit the response to the requesting computer.

In certain embodiments, the requesting computer is a pharmacy computer, the transaction is a prescription transaction, the entity identifier is a patient identifier, the identifier of the first evaluation system is a cash system identifier identifying a cash system, and the prescription transaction further comprises a prescription drug identifier. The at least one memory and the computer program code are further configured to, with the processor, cause the apparatus to determine based on at least the patient identifier, a funded benefit plan for which the patient is eligible, and to obtain the response information according to the funded benefit plan.

In certain embodiments, the alternative evaluation procedure is associated with an extended benefit. The at least one memory and the computer program code are further configured to, with the processor, cause the apparatus to provide an indication of an extended benefit to the pharmacy computer, and receive an indication from the pharmacy computer to select the extended benefit.

The at least one memory and the computer program code are further configured to, with the processor, cause the apparatus to store a plurality of historical prescription transactions as the historical data. The at least one memory and the computer program code are further configured to, with the processor, cause the apparatus to access the historical prescription transactions to identify historical data comprising the patient identifier in a subject transaction, and to determine the funded benefit plan identified in the subject transaction.

The at least one memory and the computer program code are further configured to, with the processor, cause the apparatus to at least receive the eligibility data from a computer associated with the funded benefit plan, store and maintain the eligibility data, and access the eligibility data responsive to receiving the message to determine the alternative evaluation procedure.

In certain embodiments, the prescription transaction received from the pharmacy computer does not indicate the funded benefit plan.

In certain embodiments, the alternative evaluation procedure comprises accessing a table associated with the funded benefit plan, the table comprising contractual prices based on the prescription drug identifier.

A method is also provided, the method including parsing, with a processor, a message received from a requesting computer to identify an indication of a transaction, an entity identifier, and an identifier of a first evaluation system. The method further includes evaluating the entity identifier based on at least one of historical data or eligibility data to determine an alternative evaluation procedure, performing the alternative evaluation procedure to obtain response information regarding the transaction, constructing a response to the message comprising the response information, and transmitting the response to the requesting computer.

In certain embodiments, the requesting computer is a pharmacy computer, the transaction is a prescription transaction, the entity identifier is a patient identifier, the identifier of the first evaluation system is a cash system identifier identifying a cash system, and the prescription transaction further comprises a prescription drug identifier. The method further includes determining, based on at least the patient identifier, a funded benefit plan for which the patient is eligible, and obtaining the response information according to the funded benefit plan.

The alternative evaluation procedure may be associated with an extended benefit, and the method further comprises providing an indication of an extended benefit to the pharmacy computer, and receiving an indication from the pharmacy computer to select the extended benefit.

The method further includes storing a plurality of historical prescription transactions as the historical data, accessing the historical prescription transactions to identify historical data comprising the patient identifier in a subject transaction, and determining the funded benefit plan identified in the subject transaction. The method may further include receiving the eligibility data from a computer associated with the funded benefit plan, storing and maintain the eligibility data, and accessing the eligibility data responsive to receiving the message to determine the alternative evaluation procedure.

The alternative evaluation procedure further comprises accessing a table associated with the funded benefit plan, the table comprising contractual prices based on the prescription drug identifier.

The alternative evaluation procedure is associated with an extended benefit, and the method further comprises causing transmission of pricing data and respective prescription transactions to a computer associated with the funded benefit plan.

A computer program product is provided, including at least one non-transitory computer-readable storage medium having computer-executable program code instructions stored therein, the computer-executable program code instructions comprising program code instructions to parse a message received from a requesting computer to identify an indication of a transaction, an entity identifier, and an identifier of a first evaluation system. The program code instructions may further include program code instructions to evaluate the entity identifier based on at least one of historical data or eligibility data to determine an alternative evaluation procedure. The program code instructions may further include program code instructions to perform the alternative evaluation procedure to obtain response information regarding the transaction. The program code instructions may further include program code instructions to construct a response to the message comprising the response information, and to transmit the response to the requesting computer.

In certain embodiments, the requesting computer is a pharmacy computer, the transaction is a prescription transaction, the entity identifier is a patient identifier, the identifier of the first evaluation system is a cash system identifier identifying a cash system, and the prescription transaction further comprises a prescription drug identifier. The computer-executable program code instructions further comprise program code instructions to determine based on at least the patient identifier, a funded benefit plan for which the patient is eligible, and to obtain the response information according to the funded benefit plan.

The alternative evaluation procedure is associated with an extended benefit, and the computer-executable program code instructions further comprise program code instructions to provide an indication of an extended benefit to the pharmacy computer, and receive an indication from the pharmacy computer to select the extended benefit.

The computer-executable program code instructions further comprise program code instructions to store a plurality of historical prescription transactions as the historical data, access the historical prescription transactions to identify historical data comprising the patient identifier in a subject transaction, and determine the funded benefit plan identified in the subject transaction.

An apparatus is provided, with means for parsing, with a processor, a message received from a requesting computer to identify an indication of a transaction, an entity identifier, and an identifier of a first evaluation system. The apparatus may further include means for evaluating the entity identifier based on at least one of historical data or eligibility data to determine an alternative evaluation procedure. The apparatus may further include means for performing the alternative evaluation procedure to obtain response information regarding the transaction, means for constructing a response to the message comprising the response information, and means for transmitting the response to the requesting computer.

The above summary is provided merely for purposes of summarizing some example embodiments of the invention so as to provide a basic understanding of some aspects of the invention. Accordingly, it will be appreciated that the above described example embodiments are merely examples and should not be construed to narrow the scope or spirit of the disclosure in any way. It will be appreciated that the scope of the disclosure encompasses many potential embodiments, some of which will be further described below, in addition to those here summarized.

BRIEF DESCRIPTION OF THE SEVERAL VIEWS OF THE DRAWINGS

Figure 1:
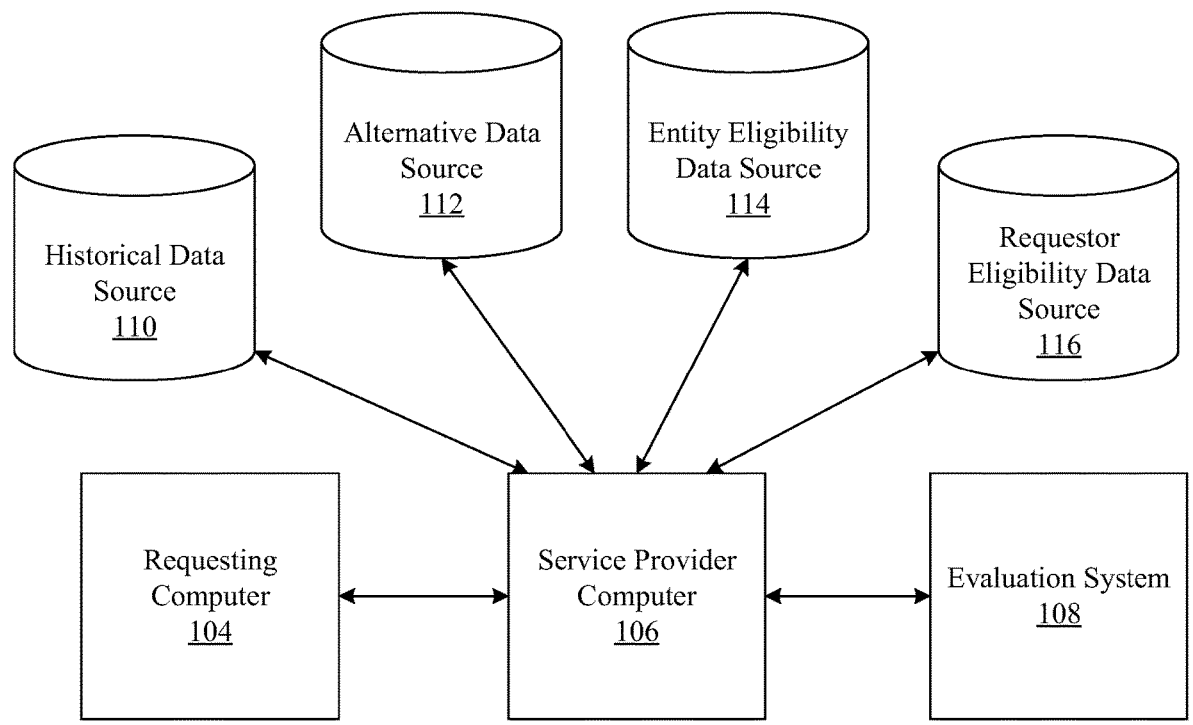
Figure 2:
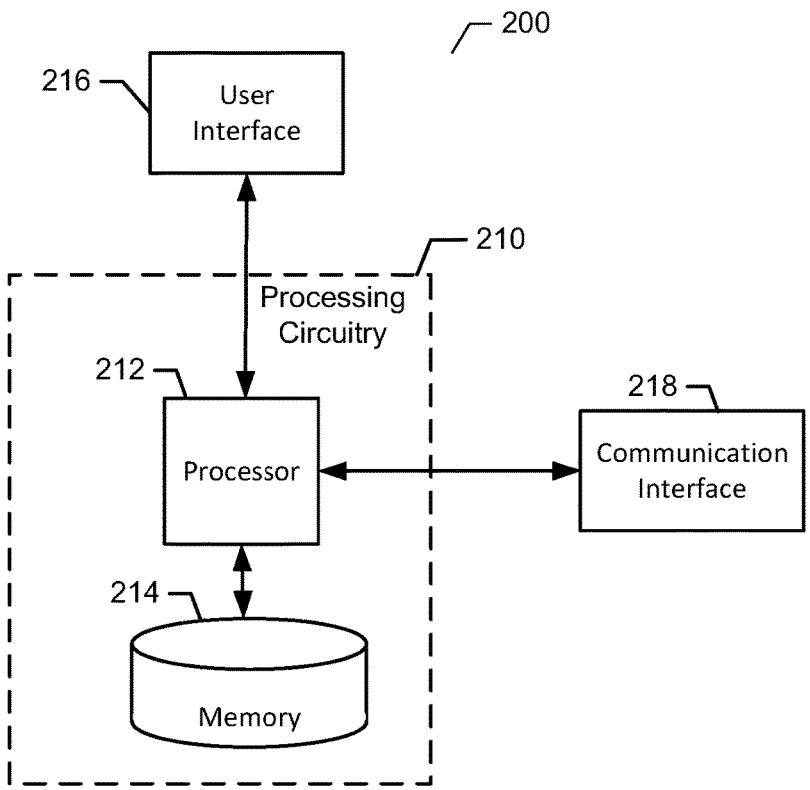
Figure 3:
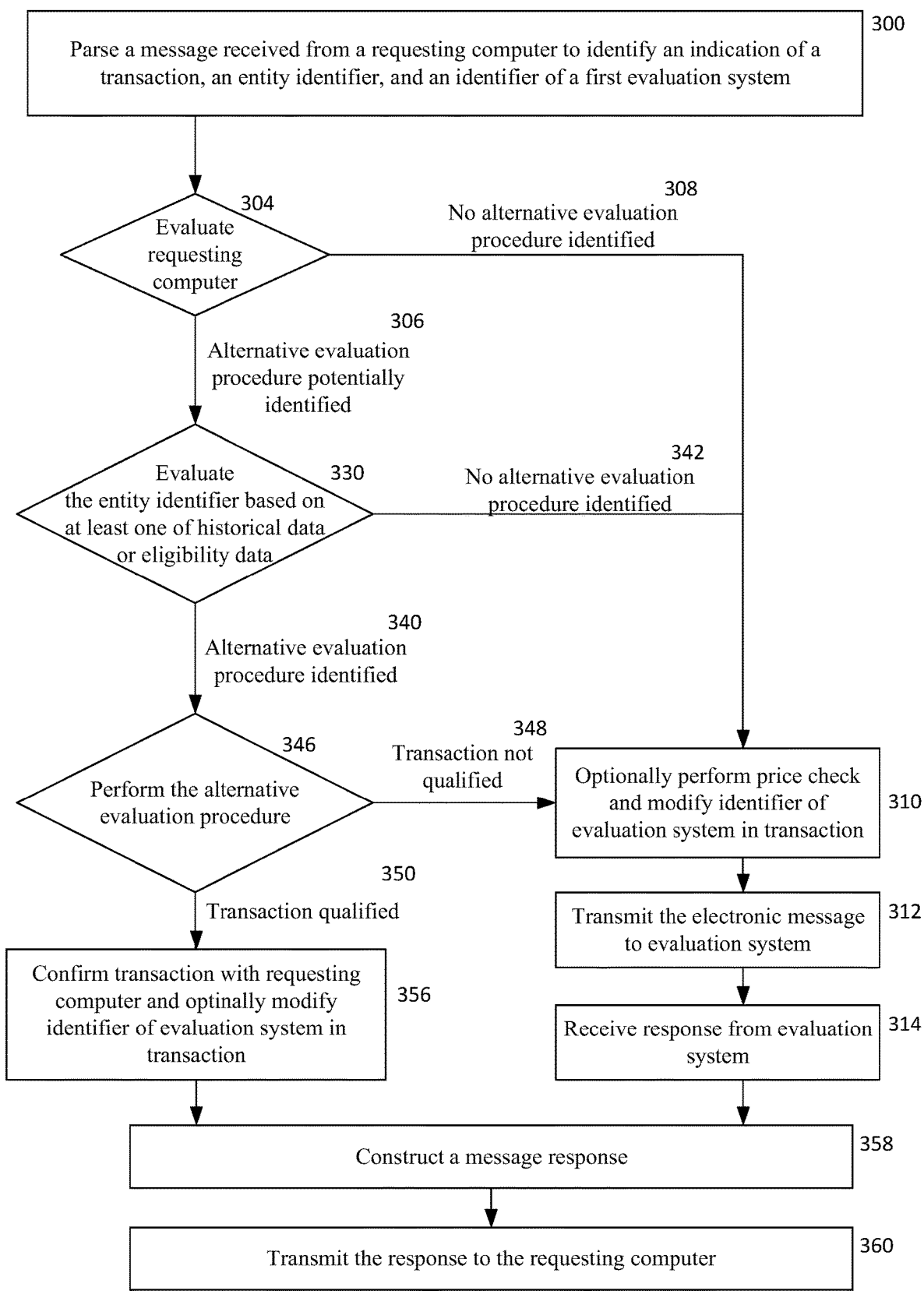

Having thus described embodiments of the invention in general terms, reference will now be made to the accompanying drawings, which are not necessarily drawn to scale, and wherein:

FIG. 1 is an example overview of a system that can be used to practice some example embodiments described herein;

FIG. 2 is an exemplary schematic diagram of an apparatus in accordance with some example embodiments; and FIG. 3 is a flowchart of operations that may be performed in accordance with some example embodiments.

DETAILED DESCRIPTION

Some embodiments of the present invention will now be described more fully hereinafter with reference to the accompanying drawings, in which some, but not all embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout.

As used herein, where a computing device is described to receive data from another computing device, it will be appreciated that the data may be received directly from the other computing device and/or may be received indirectly via one or more intermediary computing devices, such as, for example, one or more servers, relays, routers, network access points, and/or the like. Similarly, where a computing device is described herein to transmit data to another computing device, it will be appreciated that the data may be sent directly to the other computing device or may be sent to the other computing device via one or more interlinking computing devices, such as, for example, one or more servers, relays, routers, network access points, and/or the like.

FIG. 1 is an overview of a system that can be used to practice certain example embodiments. The requesting computer 104 may be any processor-driven device that facilitates the submission of messages to the service provider computer 106. Any number of requesting computers 104 may be present in a network to transmit messages to the service provider computer 106.

In certain embodiments, a requesting computer 104 may be associated with a pharmacy or pharmacy network to facilitate the filling of prescriptions, transmitting prescription claims and/or prescription transactions (and/or electronic messages associated therewith) to a service provider computer 106, and/or the like. It will be appreciated that the requesting computer 104 may be implemented as a pharmacy computer, and that references herein to a "requesting computer" may be interchanged with "pharmacy computer."

In certain example embodiments, the requesting computer 104 may be a point of sale device associated with a pharmacy. The execution of the computer-implemented instructions by the requesting computer 104 may form a special purpose computer or other particular machine that is operable to facilitate the submission of pharmacy transactions made by pharmacists, and/or the like, and the communication of information associated therewith to a service provider computer 106.

The service provider computer 106 may include, but is not limited to, a processor-driven device that is configured for receiving, processing, and responding to messages (e.g., prescription transactions) from the requesting computer 104. The service provider computer 106 may process such messages by routing them to various evaluation systems 108, or polling evaluation systems 108, described in further detail below. In certain embodiments, the service provider computer 106 may receive responses from evaluation systems 108, and return the response to a requesting computer 104 from which an associated transaction originated. Accordingly, the service provider computer 106 may be operable to facilitate the receipt, routing, and/or processing of healthcare transactions such as prescription transactions, prescription claims, and/or associated responses amongst various components and/or subsystems such as, but not limited to, those depicted in FIG. 1.

In certain exemplary embodiments, the service provider computer 106 may be configured as or may comprise a switch or router that evaluates, modifies, reformats, generates, and/or routes transactions such as healthcare transactions and prescription transactions. For example, the service provider computer 106 may route transactions communicated from a requesting computer 104 (e.g., pharmacy computer) to another computer, such as evaluation system 108 configured to return information regarding the transactions (e.g., adjudication information, co-pay information, etc.), and/or the service provider computer 106 may poll an evaluation system 108 accordingly. According to certain embodiments, the service provider computer 106 may reformat transactions into another form of transaction and/or modify the recipient information of the reformatted transaction. The service provider computer 106 may apply edits to at least some of the messages and/or transactions, and/or construct a separate message response related to messages received via the switch.

In certain embodiments, an evaluation system 108 may be associated with an adjudication computer configured to adjudicate claims on behalf of a pharmacy benefits manager (PBM), or other payer. The evaluation system 108 may comprise a computer system that receives, adjudicates, or otherwise processes a prescription claim on behalf of the payer associated with an evaluation system 108, such as the PBM. According to certain embodiments, an evaluation system may additionally or alternatively include a cash discount system, such as one other than the funded benefit plan, that the service provider computer 106 may poll to obtain cash pricing information for certain medication. Accordingly, references herein to an "evaluation system" may be interchanged with the term "cash discount system," "adjudication computer associated with a PBM," or "adjudication computer," according to certain embodiments.

The service provider computer 106 may transmit responses from the evaluation system 108 (e.g., adjudication computer) regarding the transaction, to the requesting computer 104. For example, the service provider computer 106 may notify the requesting computer 104 of out-of-pocket costs to be paid by the patient for a prescription, such as under a benefit plan and/or cash discount system associated with the evaluation system 108. In this regard, a message or other notification may be appended to or included in the response transmitted to the requesting computer 104 indicating the out-of-pocket cost, or co-pay amount. The out-of-pocket cost may be provided to the requesting computer 104 (e.g., pharmacy computer) together with a prescription transaction response, or the service provider computer 106 may reformat the prescription transaction to include the details of such responses, and transmit the reformatted healthcare transaction back to the requesting computer 104 (e.g., pharmacy computer). It will be appreciated that prescription transactions processed via a funded benefit plan may need not be routed to an evaluation system 108 or adjudication computer, because the service provider computer may store and access contract rates available under the funded benefit plan as described in further detail below.

The historical data source 110 may comprise any computing device configured to store and provide information pertaining to prescription transactions, such as but not limited to the data received in various transactions and from various requesting computers 104 and/or evaluation systems 108. For example, the historical data source 110 may be a system or database configured to track patient identifying information, and benefit plan information from previously processed prescription transactions. According to certain embodiments, the historical data source 110 may be maintained or operated by the service provider computer 106, as it functions as a switch for routing and processing certain transactions submitted by various requesting computers 104 (e.g., pharmacy computer), and the corresponding responses from evaluation computers 108 (e.g., cash discount system and/or adjudication computer associated with a PBM).

The alternative data source 112 may comprise any computing device configured to store and provide alternative information to return to a requesting computer 104, that may be different than information otherwise provided by an evaluation system 108, such as one initially indicated by the requesting computer in an electronic message. For example, if the electronic message submitted by a requesting computer 104 (e.g., pharmacy computer) indicates a particular cash discount system and/or evaluation system 108 corresponding to a cash discount system, the alternative data source 112 may provide information, such as an out-of-pocket cost under a funded benefit plan, that may differ from a cash price offered by a cash discount system and/or provided by an evaluation system 108. The alternative data may be determined based on contracted rates for a particular prescription drugs, agreed upon between a pharmacy, PBM and service provider computer 106 configured to facilitate the purchase of the prescription drugs at the contracted rates. In certain embodiments, the alternative data may comprise a list of prescription drugs that are covered under the funded benefit plan, but no pricing information may be provided. The service provider computer 106 may store and access the alternative data source 112 according to certain example embodiments provided herein.

The entity eligibility data source 114 may comprise any computing device configured to store and provide information pertaining to patient eligibility in a benefit plan and/or funded benefit plan. For example, a PBM may provide eligibility data to the service provider computer 106 for storage of the eligibility data on the entity eligibility data source 114. The eligibility data may include patient identifying information indicating patients eligibility under a certain benefit plan (and/or funded benefit plan). Various PBMs may submit eligibility data to service provider computer 106. In scenarios in which the entity eligibility data source 114 indicates eligibility in a benefit plan, a set of edibility records and/or a particular eligibility file indicating eligibility in the benefit plan, may be determined to also indicate eligibility in the funded benefit plan, such as in instances the PBM enrolls every member of the benefit plan in the funded benefit plan. Updated eligibility data may be provided on a routine basis such as monthly, annually, and/or as eligibility data changes.

Requestor eligibility data source 116 may include any computing device configured to store and provide information identifying particular requesting computers 104 (e.g., pharmacy computers, and/or pharmacies associated therewith), that participate in a funded benefit plan. The service provider computer 106 may maintain a list or table on requestor eligibility data source 116 of identifying information of pharmacies that participate in the funded benefit plan. According to certain embodiments, only a subset or some pharmacies and/or pharmacy computers configured to communicate with the service provider computer 106 participate in the funded benefit plan, such that the requestor eligibility data source 116 enables the service provider computer 106 to determine which pharmacies are eligible under or participate in the funded benefit plan.

Referring now to FIG. 2, apparatus 200 is a computing device(s) configured for implementing requesting computer 104, service provider computer 106, evaluation system 108, historical data source 110, alternative data source 112, entity eligibility data source 114, and/or requestor eligibility data source 116 according to example embodiments.

Apparatus 200 may at least partially or wholly embody or be embodied by any of the requesting computer 104, service provider computer 106, evaluation system 108, historical data source 110, alternative data source 112, entity eligibility data source 114, and/or requestor eligibility data source 116. Apparatus 200 may therefore implement any of the requesting computer 104, service provider computer 106, evaluation system 108, historical data source 110, alternative data source 112, entity eligibility data source 114, and/or requestor eligibility data source 116 in accordance with some example embodiments, or may be implemented as a distributed system that includes any of the requesting computer 104, service provider computer 106, evaluation system 108, historical data source 110, alternative data source 112, entity eligibility data source 114, requestor eligibility data source 116, and/or associated network(s).

It should be noted that the components, devices, and elements illustrated in and described with respect to FIG. 2 may not be mandatory and thus some may be omitted in certain embodiments. For example, FIG. 2 illustrates a user interface 216, as described in more detail below, which may be optional in any of the requesting computer 104 (such as when the requesting computer 104 is implemented as a service communicatively connected to a work station or other user device utilized by a pharmacist or other pharmacy employee), service provider computer 106, and/or evaluation system 108. Additionally, some embodiments may include further or different components, devices, or elements beyond those illustrated in and described with respect to FIG. 2.

Continuing with FIG. 2, processing circuitry 210 may be configured to perform actions in accordance with one or more example embodiments disclosed herein. In this regard, the processing circuitry 210 may be configured to perform and/or control performance of one or more functionalities of apparatus 200 in accordance with various example embodiments. The processing circuitry 210 may be configured to perform data processing, application execution, and/or other processing and management services according to one or more example embodiments. In some embodiments apparatus 200, or a portion(s) or component(s) thereof, such as the processing circuitry 210, may be embodied as or comprise a circuit chip. The circuit chip may constitute means for performing one or more operations for providing the functionalities described herein.

In some example embodiments, the processing circuitry 210 may include a processor 212, and in some embodiments, such as that illustrated in FIG. 2, may further include memory 214. The processing circuitry 210 may be in communication with or otherwise control a user interface 216, and/or a communication interface 218. As such, the processing circuitry 210, such as that included in any of the requesting computer 104, service provider computer 106, evaluation system 108, historical data source 110, alternative data source 112, entity eligibility data source 114, requestor eligibility data source 116, and/or apparatus 200 may be embodied as a circuit chip (e.g., an integrated circuit chip) configured (e.g., with hardware, software, or a combination of hardware and software) to perform operations described herein.

The processor 212 may be embodied in a number of different ways. For example, the processor 212 may be embodied as various processing means such as one or more of a microprocessor or other processing element, a coprocessor, a controller, or various other computing or processing devices including integrated circuits such as, for example, an ASIC (application specific integrated circuit), an FPGA (field programmable gate array), or the like. Although illustrated as a single processor, it will be appreciated that the processor 212 may comprise a plurality of processors. The plurality of processors may be in operative communication with each other and may be collectively configured to perform one or more functionalities of apparatus 200 as described herein. The plurality of processors may be embodied on a single computing device or distributed across a plurality of computing devices collectively configured to function as requesting computer 104, service provider computer 106, evaluation system 108, and/or apparatus 200. In some example embodiments, the processor 212 may be configured to execute instructions stored in the memory 214 or otherwise accessible to the processor 212. As such, whether configured by hardware or by a combination of hardware and software, the processor 212 may represent an entity (e.g., physically embodied in circuitry—in the form of processing circuitry 210) capable of performing operations according to embodiments of the present invention while configured accordingly. Thus, for example, when the processor 212 is embodied as an ASIC, FPGA, or the like, the processor 212 may be specifically configured hardware for conducting the operations described herein. Alternatively, as another example, when the processor 212 is embodied as an executor of software instructions, the instructions may specifically configure the processor 212 to perform one or more operations described herein.

In some example embodiments, the memory 214 may include one or more non-transitory memory devices such as, for example, volatile and/or non-volatile memory that may be either fixed or removable. In this regard, the memory 214 may comprise a non-transitory computer-readable storage medium. It will be appreciated that while the memory 214 is illustrated as a single memory, the memory 214 may comprise a plurality of memories. The plurality of memories may be embodied on a single computing device or may be distributed across a plurality of computing devices. The memory 214 may be configured to store information, data, applications, computer program code, instructions and/or the like for enabling apparatus 200 to carry out various functions in accordance with one or more example embodiments. For example, when apparatus 200 is implemented as service provider computer 106, memory 214 may be configured to store computer program code for performing corresponding functions thereof, as described herein according to example embodiments.

Still further, memory 214 may be configured to store routing tables, that facilitate determining the destination of communications received from a requesting computer 104, and/or evaluation system 108. Memory 214 may further include reconciliation tables for tracking the healthcare transactions received from the requesting computer 104, and reconciling them with responses received from evaluation system 108. The memory 214 may further comprise a database, such as historical data source 110, alternative data source 112, entity eligibility data source 114, and/or requestor eligibility data source 116. Still further, according to certain embodiments, the memory 214 may be modified as described herein, to reformat prescription claims and/or prescription transactions with additional information received, determined and/or generated according to example embodiments.

The memory 214 may be further configured to buffer input data for processing by the processor 212. Additionally or alternatively, the memory 214 may be configured to store instructions for execution by the processor 212. In some embodiments, the memory 214 may include one or more databases that may store a variety of files, content, or data sets. Among the contents of the memory 214, applications may be stored for execution by the processor 212 to carry out the functionality associated with each respective application. In some cases, the memory 214 may be in communication with one or more of the processor 212, user interface 216, and/or communication interface 218, for passing information among components of apparatus 200.

The optional user interface 216 may be in communication with the processing circuitry 210 to receive an indication of a user input at the user interface 216 and/or to provide an audible, visual, mechanical, or other output to the user. As such, the user interface 216 may include, for example, a keyboard, a mouse, a display, a touch screen display, a microphone, a speaker, and/or other input/output mechanisms. As such, in embodiments in which apparatus 200 is implemented as the requesting computer 104, the user interface 216 may, in some example embodiments, provide means for user entry of patient information (name, DOB, etc.), payer information (e.g., information relating to a cash discount system), details relating to the dispensing of a prescription, and/or the like. The user interface 216 may be further configured to display or provide response information such as a recommendation to submit a prescription claim under a funded benefit plan, and/or an out-of-pocket cost of prescription medications, such as when apparatus 200 is implemented as a requesting computer 104. A user of the requesting computer 104, such as a pharmacist, may then communicate with the patient regarding the information provided. In some example embodiments, aspects of user interface 216 may be limited or the user interface 216 may not be present.

The communication interface 218 may include one or more interface mechanisms for enabling communication with other devices and/or networks. In some cases, the communication interface 218 may be any means such as a device or circuitry embodied in either hardware, or a combination of hardware and software that is configured to receive and/or transmit data from/to a network and/or any other device or module in communication with the processing circuitry 210. By way of example, the communication interface 218 may be configured to enable communication amongst any of requesting computer 104, service provider computer 106, evaluation system 108, historical cash source 110, alternative data source 112, entity eligibility data source 114, requestor eligibility data source 116, and/or apparatus 200 over a network. Accordingly, the communication interface 218 may, for example, include supporting hardware and/or software for enabling wireless and/or wireline communications via cable, digital subscriber line (DSL), universal serial bus (USB), Ethernet, or other methods.

A network, such as the network in which any of the systems of FIG. 1 or components thereof or components described herein may operate, (e.g., requesting computer 104, service provider computer 106, evaluation system 108, historical data source 110, alternative data source 112, entity eligibility data source 114, requestor eligibility data source 116, apparatus 200, and/or the like) may include a local area network, the Internet, any other form of a network, or any combination thereof, including proprietary private and semi-private networks and public networks. The network may comprise a wired network and/or a wireless network (e.g., a cellular network, wireless local area network, wireless wide area network, some combination thereof, and/or the like).

FIG. 3 is a flowchart illustrating example operations of an apparatus 200, according to some example embodiments. The operations of FIG. 3 may be performed by apparatus 200, such as with the service provider computer 106, and/or the like.

As shown by operation 300, apparatus 200 may include means, such as processor 212, memory 214, user interface 216, communication interface 218, and/or the like, for parsing a message received from a requesting computer to identify an indication of a transaction, an entity identifier, and an identifier of a first evaluation system. Example embodiments may receive, from a requesting computer 104 (e.g., pharmacy computer), a message such as a prescription transaction, comprising an identifier of an evaluation system (e.g., cash discount system and/or benefit plan). The message and/or prescription transaction may further comprise a prescription identifier identifying a drug.

The message (e.g., prescription transaction) may be received from the requesting computer 104, such as following entry by a pharmacist, or other user, of data relating to a prescription drug being obtained by a patient. The patient may present a cash discount card, or information pertaining to a cash discount system, which may be entered via a user interface 216 of the requesting computer 106. Additionally or alternatively, the patient may present a benefit plan card associated with a PBM. In any event, it will be appreciated that the patient may not necessarily submit a card indicating the funded benefit plan. The identifier of the evaluation system, such as a cash discount system or benefit plan, and/or PBM, may therefore include a Bank Identification Number (BIN), Processor Control Number (PCN), Member ID, and/or Group ID.

The entity identifier may include any information pertaining to the identify of an entity such as a patient. The information may include a patient identifying information such as BIN, PCN, Member ID, and/or Group ID relating to a cash discount system and/or benefit plan. In this regard, the Member ID may uniquely identify the patient from other patients in the benefit plan. The patient identifying information may further include a pharmacy-specific identifier of the patient, patient name, patient date of birth, patient address, gender, and/or the like. The message (e.g., prescription transaction) may be received at the service provider computer 106 for further processing as described below.

As shown by operation 304, apparatus 200 may include means, such as processor 212, memory 214, communication interface 218, and/or the like, for evaluating the requesting computer 104. In this regard, only certain pharmacies may participate in funded benefit plans, such that if the message received is not from a participating pharmacy, no alternative evaluation procedure is identified. To determine legibility for a particular requesting computer 104, the processor 212 of example embodiments, such as apparatus 200, may parse the message to determine an identifier of a requesting computer 104 that transmitted the message, or the message may be received via a certain queue or feed associated with the requesting computer 104. Example embodiments may store and access a list of requesting computers 104 (e.g., pharmacy computers) and/or pharmacies associated therewith that participate in a funded benefit plan, such as via the requestor eligibility data source 116. If the requesting computer 104 from which the message was transmitted (and/or associated pharmacy) participates in a funded benefit plan, as may be indicated by the requestor eligibility data source 116, processor 212 may determine that an alternative evaluation procedure is potentially identified (306). The proceeding operations are described in further detail below.

If example embodiments determine that no alternative evaluation procedure is identified (308), such as by determining the requesting computer 104 and/or associated pharmacy does not participate in a funded benefit plan, processing may continue at operation 310, which may be optional in certain embodiments. In operation 310, if performed, apparatus 200 may include means, such as processor 212, memory 214, communication interface 218, and/or the like, for performing a price check. As a result of the price check, the indicated evaluation system, such as the first evaluation system identified in the electronic message (e.g., as initially identified by a patient and/or pharmacist and submitted via the requesting computer 104 and/or pharmacy computer), may or may not be modified in the transaction. The price check may include checking prices offered by other cash discount systems (different than the first evaluation system) for the same prescription drug indicated in the electronic message. U.S. patent application Ser. No. 16\867,286 filed May 5, 2020, and titled, "Method, Apparatus, and Computer Program Product for Constructing Electronic Message Responses Dependent Upon Historical Information," describes certain methods, systems, and/or the like for performing a price check, and is hereby incorporated by reference in its entirety. Example embodiments, such as apparatus 200 may perform the price check by accessing historical transactions associated with the prescription drug and various cash discount systems. In such examples, if a different cash discount system is identified as providing a better or lower price, relative to a price provided by the first evaluation system identified according to the electronic message (and as indicated in historical transactions), in certain embodiments, the apparatus 200 may optionally provide a response to the requesting computer 104 (e.g., pharmacy computer) indicating the different pricing options and systems, and optionally enable selection at the pharmacy computer of the evaluation system 108 (e.g., cash discount system) selected by the patient and/or pharmacist.

In any event, as shown in operation 312, apparatus 200 may include means, such as processor 212, memory 214, communication interface 218, and/or the like, for transmitting the electronic message to an evaluation system 108, such as the first evaluation system (or optionally a different cash discount system identified according to the price check described above). In this regard, the service provider computer 106 processes and routes the prescription transaction to the selected cash discount system, whether the cash discount system is initially provided by or selected by the patient, and/or modified according to the above described price check system. In certain scenarios such as those in which the patient presented or selected benefit plan information (e.g., an insurance card), the first evaluation system may be an adjudication computer associated with a PBM.

As shown in operation 314, apparatus 200 may include means, such as processor 212, memory 214, communication interface 218, and/or the like, for receiving a response from the evaluation system. In this regard, receiving a response from the evaluation system (e.g., cash discount system and/or adjudication computer associated with a PBM) provides or confirms the out-of-pocket cost the patient will pay for the prescription drugs (whereas the optional price check that may have been previously performed estimates the out-of-pocket cost based on historical transactions). In this regard, in some scenarios, the price check performed may result in a same out-of-pocket cost as returned by the evaluation system in operation 314. In any event, responses received from a plurality of evaluation systems 108 (e.g., adjudication computer), such as over a switch, may be processed and reconciled with their associated prescription claims (transmitted to the service provider computer 106 by a requesting computer 104), such that the response can be constructed and returned to the requesting computer 104 as described in further detail below.

Returning to outcome 306 of operation 304, if an alternative evaluation proceeded is potentially identified, such as in response to determining the requesting computer 104 (e.g., pharmacy computer) from which the message is received participates in a funded benefit plan, at operation 330, apparatus 200 may include means, such as processor 212, memory 214, communication interface 218, and/or the like, for evaluating the entity identifier based on at least one of historical data or eligibility data. Example embodiments may therefore access historical data source 110 to determine whether there are prior prescription claims associated with the entity identifier (e.g., patient identifier and/or the like). If a prescription claim relating to the patient is identified, processor 212 of example embodiments, such as apparatus 200, may further process the identified prescription claim to determine a benefit plan and/or funded benefit plan associated with the prescription claim. If a funded benefit plan is identified in a related historical prescription claim, example embodiments may determine the patient is eligible under the funded benefit plan and a corresponding alternative evaluation procedure is therefore identified. If a benefit plan is identified as associated with a historical prescription claim associated with the patient, and the benefit plan is associated with a funded benefit plan (e.g., the PBM of the benefit plan sponsors a funded benefit plan, in which member of the benefit plan are also enrolled), example embodiments determine that the patient associated with the electronic message is eligible under the funded benefit plan, such that an alternative evaluation procedure is identified (340).

In addition to, or instead of accessing historical data to determine eligibility under a funded benefit plan, example embodiments, such as processor 212 of apparatus 200 may access eligibility data, such as via entity eligibility data source 114, to determine whether an alternative evaluation procedure is identified (e.g., whether the patient qualifies for the funded benefit plan). Example embodiments may access the eligibility data to determine whether the entity identifier (e.g., patient identifier) is present in an eligibility file and/or eligibility record for a benefit plan and/or funded benefit plan. If the eligibility file indicates the patient is eligible under a benefit plan, and the benefit plan is associated with a funded benefit plan (e.g., the PBM of the benefit plan sponsors a funded benefit plan, in which member of the benefit plan are also enrolled), example embodiments determine that the patient associated with the message (e.g., prescription transaction) is eligible under the funded benefit plan, and an alternative evaluation procedure is therefore identified. Additionally, or alternatively, an eligibility file for a funded benefit plan (which may be different than an eligibility file indicating eligibility under a benefit plan) may indicate eligibility. In any event, example embodiments may determine by accessing the entity eligibility data source 114, whether the patient is eligible under a funded benefit plan, and as such, whether an alternative evaluation procedure is identified.

According to certain embodiments, one of the historical data or the eligibility data may be accessed to determine eligibility. In certain embodiments, both historical data and eligibility data may be accessed to determine eligibility, and if either source indicates eligibility, the processor 212 determines the patient associated with the message is eligible under the identified funded benefit plan. In this regard, if example embodiments determine the patient is eligible under the identified funded benefit plan, an alternative evaluation procedure is identified (340). If it is determined the patient is not enrolled in, or does not qualify for a funded benefit plan, no alternative evaluation procedure is identified (342), and processing continues to optional operation 310 as described above.

In operation 346, in response to determining an alternative evaluation procedure is identified (e.g., the requesting computer 104 and/or pharmacy from which the message originated participates in a funded benefit plan, and the entity identifier associated with the message (e.g., an identifier of a patient) is associated with the funded benefit plan), apparatus 200 may include means, such as processor 212, memory 214, communication interface 218, and/or the like, for performing the alternative evaluation procedure.

Performing the alternative evaluation procedure may comprise determining whether the transaction (e.g., prescription transaction) indicated in the message indicates a prescription identifier that qualifies the transaction under the funded benefit plan and if so, returning the contracted price of the prescription drug. In this regard, processor 212 of apparatus 200 accesses the alternative data source 112, to determine whether the prescription drug identified in the message (e.g., transaction, or prescription transaction), is indicated as covered under the funded benefit plan. In this regard, the alternative data source 112 indicates response information, such as a contracted price, for which the patient may obtain the prescription drug at the pharmacy.

The alternative data source 112 may in some instances indicate a generic code number (GCN) of a prescription drug, generic product identifier (GPI), or an NDC (National Drug Code) of a prescription drug that qualifies under the funded benefit plan for an extended benefit. The GCN or GPI may indirectly identify a group of medications whereas an NDC may identify a single prescription drug. When a GCN or GPI is indicated, example embodiments may reference a standards table and/or the like to determine what NDCs are included in a group of medications defined by a GCN or GPI. In any event, based on the prescription identifier provided in the prescription transaction (e.g., NDC), example embodiments determine whether the prescription drug is covered under the funded benefit plan.

In certain embodiments, performing the alternative evaluation procedure may comprise determining whether the transaction (e.g., prescription transaction) indicated in the message indicates a prescription identifier that qualifies the transaction under the funded benefit plan, but determining a contract price is not predefined or is not available, and if so, calculating the out-of-pocket cost of the prescription drug so to match an out-of-pocket cost that may be obtainable via a different system, such as a different cash discount system or evaluation system such as the first evaluation system. U.S. patent application Ser. No. 16/792,413 filed Feb. 17, 2020 and titled, "Method, Apparatus and Computer Program Product for Partitioning Prescription Transaction Costs in an Electronic Prescription Transaction," describes some methods and systems for dynamically calculating an out-of-pocket cost to match (e.g., equal) or be less than a different price obtainable via a different system, and is hereby incorporated by reference in its entirety. For example, example embodiments may determine an extended benefit amount by utilizing a price returned by a different evaluation system 108 (e.g., adjudication computer, PBM and/or the like), such as the first evaluation system provided in the message (e.g., the cash discount system identified by the patient and/or requesting computer 104). Application Ser. No. 16/792,413 describes that a credit amount can be applied to a prescription transaction such that an out-of-pocket cost otherwise charged to the patient under a cash discount system, such as the first evaluation system, can be matched. Matching the price of another cash discount system may encourage patients to utilize the benefit plan and/or funded benefit plan associated with the PBM, such that the PBM can monitor prescription adherence by a patient. In this regard, response information such as the out-of-pocket cost a patient would pay under the funded benefit plan may be matched to a price otherwise obtainable via a cash discount system. In this regard, in certain embodiments, the response information may be dynamically calculated to match the determined price, but such that a credit amount does not exceed a threshold amount set by a contract for the funded benefit plan defined by the service provider computer 106 and the PBM.

In any event, if an out-of-pocket cost is determined under the funded benefit plan (whether referenced as a contract price, and/or dynamically calculated), processor 212 of apparatus 200 may perform a pre-edit on the transaction (e.g., prescription transition) to include the out-of-pocket price that would be paid by the patient under the funded benefit plan. The pre-edit may further include an indicator that a change to the funded benefit plan, rather than the first evaluation system, may be recommended.

If the prescription drug is not on a contracted list indicated by the alternative data source 112, processor 212 determines the transaction is not qualified (348) (e.g., not qualified under the funded benefit plan), and may optionally perform a price check at operation 310.

In operation 356, apparatus 200 may include means, such as processor 212, memory 214, user interface 216, communication interface 218, and/or the like, for confirming the transaction with the requesting computer 106, and modifying an identifier of the evaluation system in the transaction, if confirmed by the requesting computer 104. In this regard, example embodiments may prevent the transaction from being further routed to an evaluation system and/or adjudication computer until a response is received from the requesting computer 106 either confirming or selecting the evaluation system to be used to process the transaction. Example embodiments may therefore cause display of an indication of the funded benefit plan to the requesting computer 104 (e.g., pharmacy computer), and indicate that the prescription transaction, including the patient obtaining the prescription, may qualify under the funded benefit plan, and may further indicate the price for the prescription drug under the funded benefit plan. The response may further indicate that the price is lower than a price obtained via the first evaluation system (e.g., cash discount system) indicated in the message (e.g., prescription transaction). In certain embodiments, the information displayed may include multiple or all pricing options and respective evaluation systems, cash discount systems, benefit plan, and/or the like. In this regard, the service provider computer 106 may await an indication from the pharmacy computer to select the extended benefit provided via the funded benefit plan, and once received, continue processing in operation 358. The service provider computer 106 may receive a confirmation and/or selection of the funded benefit plan, and modify or update the identifier of the evaluation system in the transaction as indicated by the requesting computer 104. In certain embodiments, the modification and/or update to the evaluation system may occur with respect to operation 346, but may be further modified if indicated differently by the requesting computer 104 in operation 356. As another option as an outcome to operation 356, (not illustrated), the requesting computer may decline a recommendation to select the funded benefit plan or select a different option, and processing may continue to operation 310 and/or 312 to proceed with a different evaluation system, such as evaluation system 108 indicated by the requesting computer 108.

In operation 358, apparatus 200 may include means, such as processor 212, memory 214, communication interface 218, and/or the like, for constructing a message response comprising the response information. In the instance a prescription qualifies under the funded benefit plan, and the requesting computer 104 (e.g., pharmacy computer) confirms to select the funded benefit plan, the response information includes the contract price to be paid by the patient under the funded benefit plan (which may already have been confirmed by the patient and/or pharmacist via the requesting computer 104). On the other hand, a response returned by a different cash discount system selected by the requesting computer 104 (e.g., pharmacy computer) may be included in the response information.

In operation 360, apparatus 200 may include means, such as processor 212, memory 214, communication interface 218, and/or the like, for transmitting the response to the requesting computer 104 (e.g., pharmacy computer). The requesting computer 104 may then display the response indicating the payment required by the patient (which in many scenarios will match a pricing option selected via the requesting computer 104 with respect to operation 356). Accordingly, a pharmacist may complete the transaction with the patient, process payment, and distribute the prescription drug.

In an instance in which a transaction is performed via the funded benefit plan, apparatus 200 may include means, such as processor 212, memory 214, communication interface 218, and/or the like, for transmitting such transactions to the PBM associated with, or that is a sponsor of, the funded benefit plan. The PBM may therefore have visibility to adherence by patients, even in regards to cash transactions that may not otherwise be routed to the PBM, and may adjust or assess internal metrics such as a generic dispense rate (GDR) accordingly. Similarly, the PBM in optional coordination with the pharmacy may adjust the contract pricing of certain prescription drugs under the funded benefit plan. The transaction details associated with prescription transactions processed via the funded benefit plan may be forwarded to or transmitted to a computer associated with the PBM on a predetermined routine basis and/or in real-time or near real-time as the transactions are processed by the service provider computer 106.

According to example embodiments provided herein, a patient and/or pharmacist may be alerted, in real-time or near real-time as a prescription transaction is submitted, of eligibility under a funded benefit plan. As used herein, the terms real-time and near real-time indicate a seemingly instant response time, such that a patient obtaining a prescription may obtain pricing information and the out-of-pocket amount, as the pharmacist or other employee interacts with a user interface 216 of the requesting computer 104 or a user interface 216 in communication with the requesting computer 104. Similarly, the requesting computer 104 may receive a message (such as a message requesting selection, and/or a message indicating a confirmation) from the service provider computer 106 in real-time or near real-time relative to when a message (e.g., prescription transaction) is transmitted to the service provider computer 106. It will be appreciated that despite the reference to real-time or near real-time, certain delays based on computer processing time may be encountered. Performing certain operations provided herein in real-time or near real-time may ensure the patient is informed regarding the funded benefit plan and extended benefit while the patient is obtaining the prescription at the pharmacy, and that the prescription transaction may be optionally prevented from being submitted to the first evaluation system.

Redirecting the prescription transaction to utilize the funded benefit plan may benefit pharmacies, as their profit margins may be increased based on the contract pricing under the funded benefit plan. The cost to the patient may also be decreased relative to what would otherwise be obtained via the cash discount system initially indicated. Moreover, the PBM may benefit by having insight to the prescription transactions redirected to the funded benefit plan by the service provider computer 106, whereas the PBM may not otherwise have visibility to prescription claims submitted to the service provider computer 106 and routed to the first evaluation system as initially indicated in the message (e.g., prescription transaction).

Example embodiments provided herein therefore provide a technical solution to the technical problem presented by networked-based service provider computers interfacing with evaluation systems. In many implementations, such as those that don't employ example embodiments provided herein, messages are only routed or forwarded to an evaluation system identified in the message. Example embodiments utilize historical information and/or eligibility data to perform alternative evaluation procedures and potentially route the message to different recipients than to which the transaction would be routed based on the originally received message. In this regard, different or improved information may be included in a message response. Accordingly, example embodiments perform alternative evaluation procedures to provide improved information.

Example embodiments are further integrated into a practical application of dynamically routing and modifying prescription transactions, to provide improved information to the patient and/or pharmacy. This application in the area of prescription transactions provides an improvement to the existing technology of prescription claims processing and service provider computers.

Without the advantages of the present disclosure, patients and/or pharmacists may have to submit multiple prescription inquiries and/or transactions with the pharmacist to determine various pricing options. Accordingly, example embodiments improve the technology of prescription claims processing and service provider computers by providing the improvement to the stakeholders including patients and pharmacies. Additionally, based on the reduced or limited need to submit multiple prescription inquiries for the same prescription transaction, example embodiments reduce or limit the processing resources, network resources, and memory resources otherwise required to facilitate the processing, routing, and completion of the otherwise submitted multiple prescription inquiries for the same transaction to "test" the pricing schemas and identify a good price or best price (e.g., for the patient and/or pharmacy). Additionally or alternatively, a pharmacy may save money it is otherwise charged for switching fees to determine which option is the best option for the patient.

Moreover, in addition to reducing the number of additional claims that may otherwise be submitted to test pricing under different evaluation systems, certain systems may need to process transaction reversals, to indicate to certain evaluation systems that some or all of the transactions initially submitted, such as those to test the price of a prescription drug, will not be finalized or approved for further routing. Reversals require additional processing, network, and memory resources to be routed and processed, such that example embodiments provided herein may reduce the number of reversals otherwise required to reverse transactions only submitted to "test" the price, and may therefore reduce the required processing and memory resources that would otherwise be expended on the facilitation, processing and routing of reversal transactions. The reduction in the utilization of such resources may be realized by the requesting computer 104, service provider computer 106, and/or evaluation system 108.

It will be appreciated that the figures are each provided as examples and should not be construed to narrow the scope or spirit of the disclosure in any way. In this regard, the scope of the disclosure encompasses many potential embodiments in addition to those illustrated and described herein. Numerous other configurations may also be used to implement embodiments of the present invention.

FIG. 3 illustrates operations of a method, apparatus, and computer program product according to some example embodiments. It will be understood that each operation of the flowchart or diagrams, and combinations of operations in the flowchart or diagrams, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may comprise one or more memory devices of a computing device (for example, memory 214) storing instructions executable by a processor in the computing device (for example, by processor 212). In some example embodiments, the computer program instructions of the computer program product(s) which embody the procedures described above may be stored by memory devices of a plurality of computing devices. As will be appreciated, any such computer program product may be loaded onto a computer or other programmable apparatus (for example, apparatus 200) to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product may comprise an article of manufacture which implements the function specified in the flowchart block(s). The computer program instructions of one or more computer program products may also be loaded onto a computer or other programmable apparatus (for example, apparatus 200 and/or other apparatus) to cause a series of operations to be performed on the computer or other programmable apparatus to produce a computer-implemented process such that the instructions which execute on the computer or other programmable apparatus implement the functions specified in the flowchart block(s).

Accordingly, blocks of the flowchart support combinations of means for performing the specified functions and combinations of operations for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. An apparatus comprising at least one processor and at least one memory including computer program code, the at least one memory and the computer program code configured to, with the processor, cause the apparatus to at least:

parse a message received from a pharmacy computer to identify an indication of a prescription transaction, a patient identifier, a prescription drug identifier and an identifier of a cash discount system, wherein the prescription transaction received from the pharmacy computer does not indicate a funded benefit plan;

in real-time or near real-time relative to receiving the message, evaluate the patient identifier based on at least one of historical data or eligibility data to determine a funded benefit plan in which a patient is eligible for an extended benefit;

access information associated with the funded benefit plan to determine a contractual price for a prescription drug identified by the prescription drug identifier;

construct a response to the message comprising the contractual price and an indication of the extended benefit associated with the funded benefit plan;

transmit the response to the pharmacy computer;

receive an indication from the pharmacy computer to select the extended benefit rather than the cash discount system;

prevent the prescription transaction from being routed to the cash discount system; and cause transmission of the prescription transaction to a computer associated with the funded benefit plan.

2. The apparatus according to claim 1, wherein the at least one memory and the computer program code are further configured to, with the processor, cause the apparatus to at least:
store a plurality of historical prescription transactions as the historical data; and
access the historical prescription transactions in real-time or near real-time responsive to receiving the message to determine the funded benefit plan in which the patient is eligible for the extended benefit.

3. The apparatus according to claim 1, wherein the at least one memory and the computer program code are further configured to, with the processor, cause the apparatus to at least:
receive the eligibility data from a computer associated with the funded benefit plan;
store and maintain the eligibility data; and
access the eligibility data in real-time or near real-time responsive to receiving the message to determine the funded benefit plan in which the patient is eligible for the extended benefit.

4. The apparatus according to claim 1, wherein the at least one memory and the computer program code are further configured to, with the processor, cause the apparatus to at least:
cause transmission of pricing data and respective prescription transactions to a computer associated with the funded benefit plan.

5. The apparatus according to claim 1, wherein causing transmission of the prescription transaction to the computer associated with the funded benefit plan facilitates visibility of adherence related to non-insurance prescription transactions.

6. A method comprising:
parsing, with a processor, a message received from a pharmacy computer to identify an indication of a prescription transaction, a patient identifier, a prescription drug identifier and an identifier of a cash discount system, wherein the prescription transaction received from the pharmacy computer does not indicate a funded benefit plan;

in real-time or near real-time relative to receiving the message, evaluating the patient identifier based on at least one of historical data or eligibility data to determine a funded benefit plan in which a patient is eligible for an extended benefit;

accessing information associated with the funded benefit plan to determine a contractual price for a prescription drug identified by the prescription drug identifier;

constructing a response to the message comprising the contractual price and an indication of the extended benefit associated with the funded benefit plan;

transmitting the response to the pharmacy computer;

receiving an indication from the pharmacy computer to select the extended benefit rather than the cash discount system;

preventing the prescription transaction from being routed to the cash discount system; and causing transmission of the prescription transaction to a computer associated with the funded benefit plan.

7. The method according to claim 6, further comprising:
storing a plurality of historical prescription transactions as the historical data;
accessing the historical prescription transactions in real-time or near real-time responsive to receiving the message to determine the funded benefit plan in which the patient is eligible for the extended benefit; and
determining the funded benefit plan identified in the subject transaction.

8. The method according to claim 6, further comprising:
receiving the eligibility data from a computer associated with the funded benefit plan;
storing and maintain the eligibility data; and
accessing the eligibility data in real-time or near real-time responsive to receiving the message to determine the funded benefit plan in which the patient is eligible for the extended benefit.

9. The method according to claim 6, wherein the method further comprises:
causing transmission of pricing data and respective prescription transactions to a computer associated with the funded benefit plan.

10. The method according to claim 6, wherein causing transmission of the prescription transaction to the computer associated with the funded benefit plan facilitates visibility of adherence related to non-insurance prescription transactions.

11. A computer program product comprising at least one non-transitory computer-readable storage medium having computer-executable program code instructions stored therein, the computer-executable program code instructions comprising program code instructions to:
parse a message received from a pharmacy computer to identify an indication of a prescription transaction, a patient identifier, a prescription drug identifier and an identifier of a cash discount system, wherein the prescription transaction received from the pharmacy computer does not indicate a funded benefit plan;

in real-time or near real-time relative to receiving the message, evaluate the patient identifier based on at least one of historical data or eligibility data to determine a funded benefit plan in which a patient is eligible for an extended benefit;

access information associated with the funded benefit plan to determine a contractual price for a prescription drug identified by the prescription drug identifier;

construct a response to the message comprising the contractual price and an indication of the extended benefit associated with the funded benefit plan;

transmit the response to the pharmacy computer;

receive an indication from the pharmacy computer to select the extended benefit rather than the cash discount system;

prevent the prescription transaction from being routed to the cash discount system; and cause transmission of the prescription transaction to a computer associated with the funded benefit plan.

12. The computer program product according to claim 11, wherein the computer-executable program code instructions further comprise program code instructions to:

store a plurality of historical prescription transactions as the historical data; and access the historical prescription transactions in real-time or near real-time responsive to receiving the message to determine the funded benefit plan in which the patient is eligible for the extended benefit; and determine the funded benefit plan identified in the subject transaction.

13. The computer program product according to claim 11, wherein the computer-executable program code instructions further comprise program code instructions to:

receive the eligibility data from a computer associated with the funded benefit plan;

store and maintain the eligibility data; and access the eligibility data in real-time or near real-time responsive to receiving the message to determine the funded benefit plan in which the patient is eligible for the extended benefit.

14. The computer program product according to claim 11, wherein causing transmission of the prescription transaction to the computer associated with the funded benefit plan facilitates visibility of adherence related to non-insurance prescription transactions.

* * * * *